United States Patent [19]

Laska et al.

[11] Patent Number: 5,104,808
[45] Date of Patent: Apr. 14, 1992

[54] METHOD AND APPARATUS FOR EFFECTING A PLURALITY OF ASSAYS ON A PLURALITY OF SAMPLES IN AN AUTOMATIC ANALYTICAL DEVICE

[76] Inventors: Paul F. Laska, 510 Wyndham Rd., Wilmington, Del. 19809; Kyoko Imai, Ichige 622-23, Katsuta, Ibaraki, Japan; Hiroshi Hashimoto, Tokai 1616, Nakagun, Ibaraki, Japan; Hajime Betsui, Tahiko 1409-2;. Hiroshi Umetsu, Tsuda 2153-27, both of Katsuta, Ibaraki, Japan

[21] Appl. No.: 237,119

[22] Filed: Aug. 26, 1988

[51] Int. Cl.[5] ............... G01N 35/02; C12M 1/40; C12M 1/36; G05B 17/00
[52] U.S. Cl. .................................. 436/48; 436/50; 422/50; 422/63; 422/64; 422/67; 422/116; 435/7.92; 435/288; 435/289
[58] Field of Search ............ 435/289, 312, 7.1–7.92, 435/288, 291; 436/47, 48, 49, 50, 808; 422/62, 63, 64, 67, 50, 116

[56] References Cited

U.S. PATENT DOCUMENTS

| | | | |
|---|---|---|---|
| 4,197,337 | 4/1980 | Di Biasi et al. | 427/270 |
| 4,276,051 | 6/1981 | Ginsberg et al. | 436/47 |
| 4,315,891 | 2/1982 | Sakurada | 422/64 |
| 4,451,433 | 5/1984 | Yamashita et al. | 422/63 |
| 4,459,265 | 7/1984 | Berglund | 422/64 |
| 4,661,408 | 4/1987 | Lau et al. | 428/405 |
| 4,803,050 | 2/1989 | Mack | 422/65 |
| 4,908,186 | 3/1990 | Sakamaki | 422/64 |

OTHER PUBLICATIONS

C. G. Hedin, Biotech Bioeng. Symp. No. 3 (1972) 172–174.
P. J. Robinson et al., Biotech Bioeng. (1973) 15, 603–609.
P. Dunhill et al., Biotech Bioeng. (1974) 10, 987–990.
M. Horisberger, Biotech Bioeng., (1976) 18, 1645–1651.

Primary Examiner—David L. Lacey
Assistant Examiner—William K. Y. Chan

[57] ABSTRACT

A diagnostic instrument and method indexes plural, sequentially actuated reaction vessels, stepwise to several processing positions. Several positions effecting wash have wash probes that are gauged together. Sample and/or reagent are not added to a number of vessels leading and trailing sample containing vessels. The processing of the sample is controlled according to different time-templates and the first use of the wash probes occurs in the same cycle for different sets of analytical tests.

4 Claims, 14 Drawing Sheets

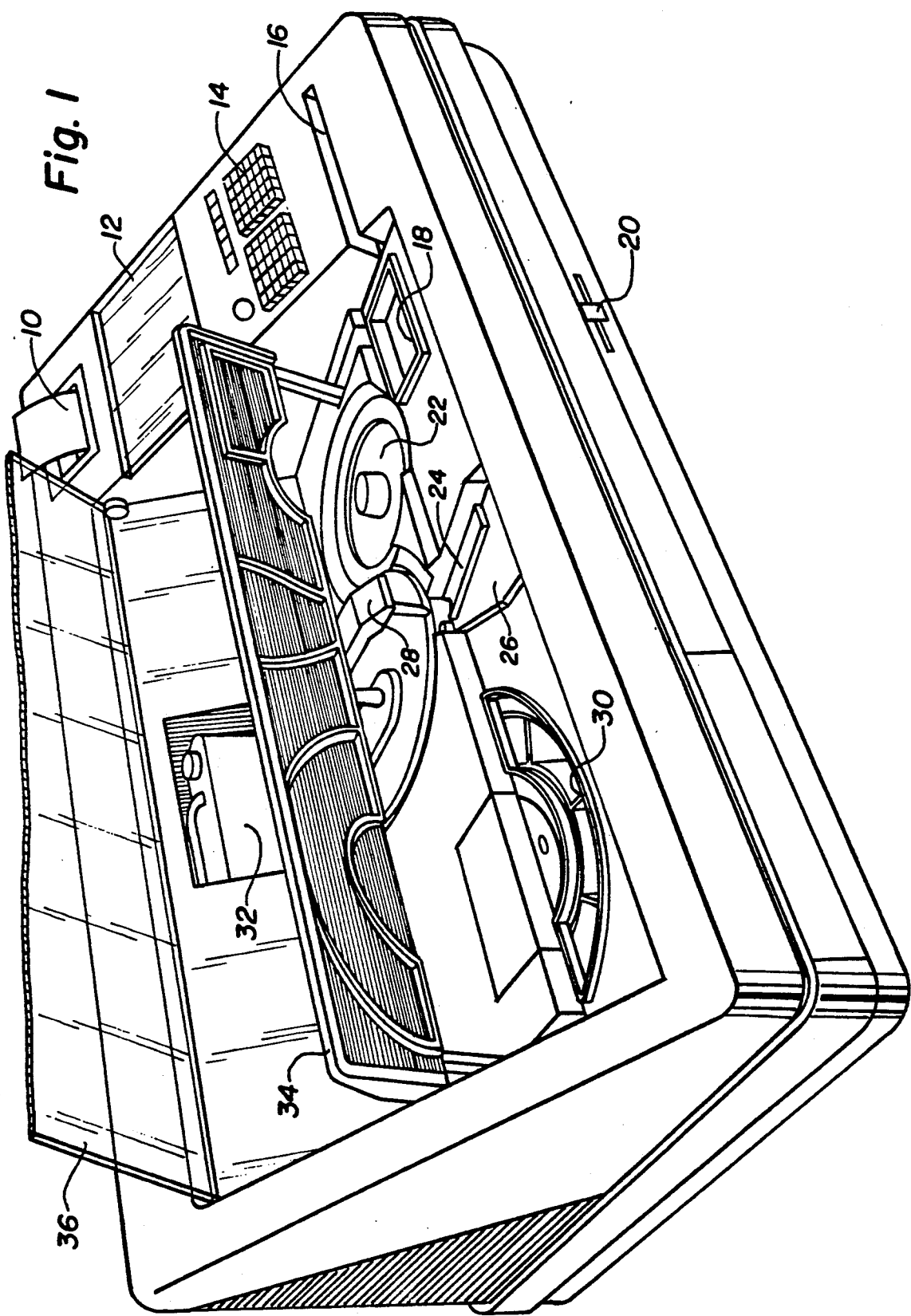

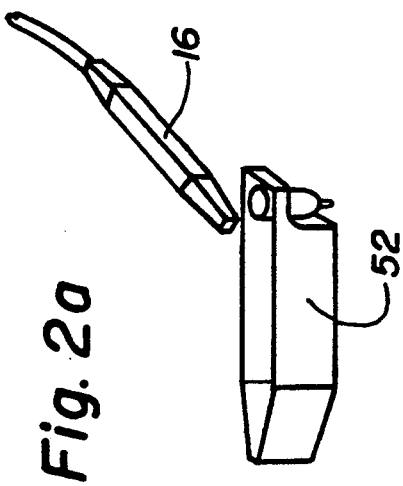
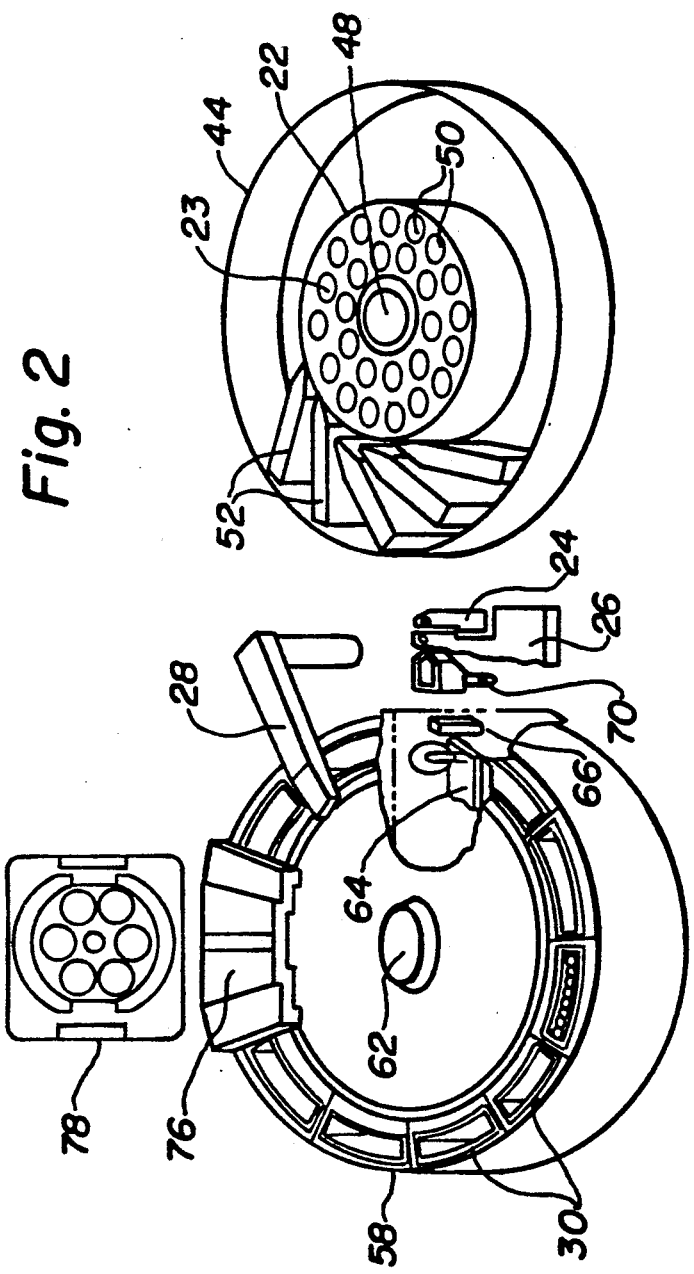

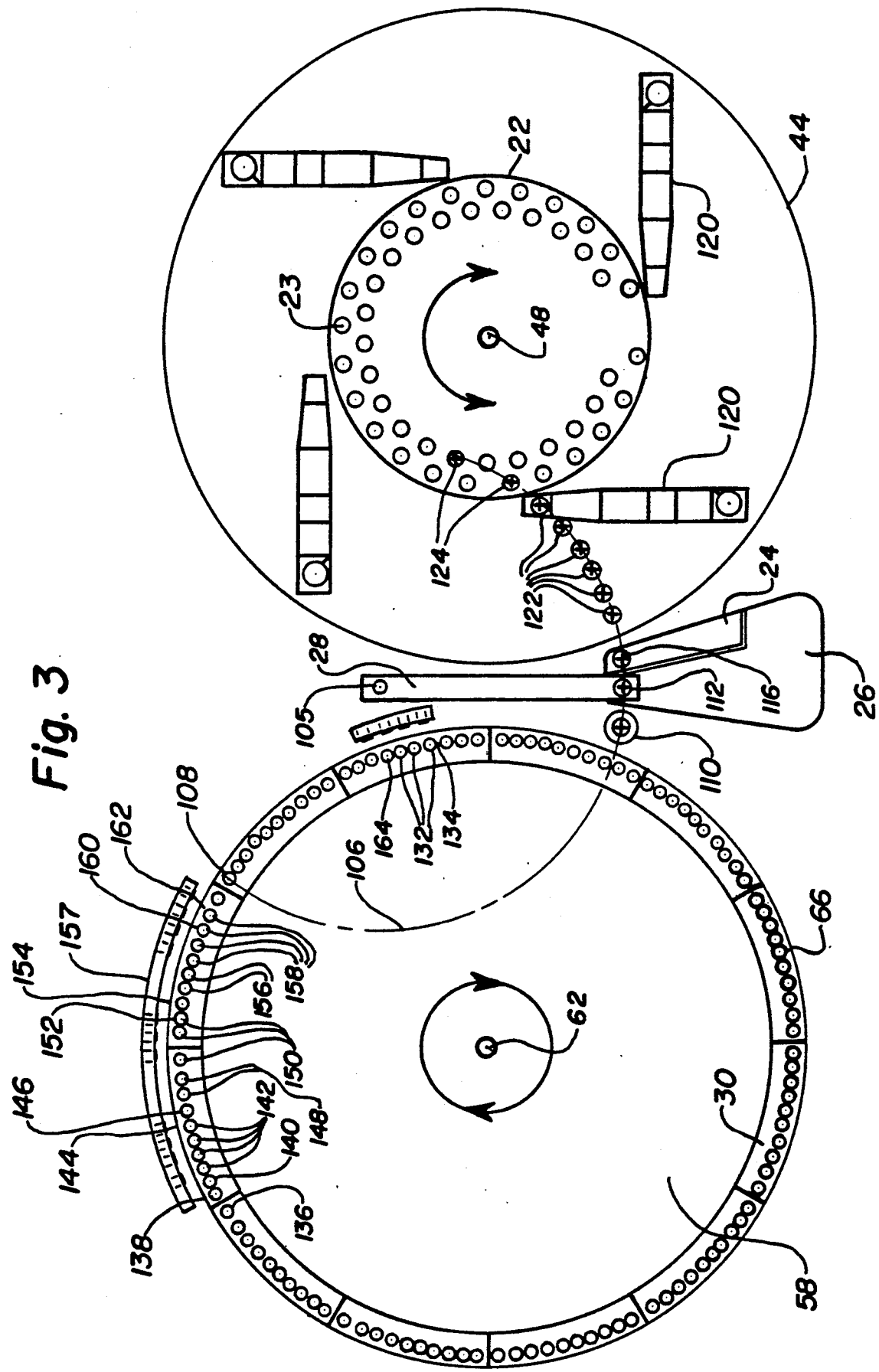

METHOD AND APPARATUS FOR EFFECTING A PLURALITY OF ASSAYS ON A PLURALITY OF SAMPLES IN AN AUTOMATIC ANALYTICAL DEVICE

CROSS REFERENCE TO RELATED APPLICATION

Subject matter disclosed herein is disclosed for Automatically Processing Magnetic Solid Phase Reagents, filed Aug. 10, 1988, Ser. No. 07/230,449, commonly assigned.

FIELD OF THE INVENTION

The present invention relates to an automated apparatus for analyzing liquid samples, particularly for quantitatively determining the presence of a variety of substances including antibodies, antigens and various proteins including cancer markers and hormones in a biological samples. In particular, the present invention provides a means to automatically perform any of a variety of assays on a plurality of samples in a single batch wherein a plurality of analytical protocols are employed. An analytical protocol is defined as that sequence of process steps to be carried out at specific times by specific hardware resources for each sample to be analyzed using the protocol.

BACKGROUND OF THE INVENTION

There are numerous automatic clinical analysis type instruments available on the market today. Typical of these is the Automatic Clinical Analyzer known as the aca® sold by E. I. du Pont de Nemours & Co., Inc. This is an instrument in which the incubator is a belt or chain in which a sample, associated with reagent packs, is analyzed for its various components. While quite satisfactory for many purposes it does not have the versatility required for some of the more recently developed immunoassay type tasks. Other machines that are available are those that are described, for example, in U.S. Pat. No. 4,315,891 assigned to Olympus Optical Company. This patent also deals with a belt or chain incubator instrument and has a single reaction line in which reaction vessels are carried step by step along the reaction line. Samples and reagents are delivered to the vessels during their movement along the reaction line to obtain a test liquid which is then subjected to photometric analysis. This machine permits several tests to be run simultaneously on samples by an interleaving processing. Unfortunately, this apparatus does not have the capability for performing the precise washing required in heterogeneous immunoassays. Another automatic analytical apparatus is that described in U.S. Pat. No. 4,459,265 assigned to Clinicon. This apparatus includes a stepwise rotatable circular plate. It carries a plurality of reaction tubes on its periphery with several reagent supply stations arranged at different locations around such periphery. The use of multiple stations does provide the machine with the versatility to carry out several different test methodologies, but again does not provide the necessary washing required for heterogeneous immunoassays.

Such heterogeneous immunoassays typically are performed using a solid support, preferably with the solid support being formed from magnetic particles. A particularly preferred support for this purpose is that described in U.S. Pat. No. 4,661,408 assigned to E. I. du Pont de Nemours & Co., Inc. This patent describes a chromium dioxide particle which has favorable magnetic properties for use as a solid support in such assays.

The concept of using magnetically responsive particles to effect separations of bioactive materials is old in the art (Hedin, C. G., Biotech. Bioeng. Symp. No. 3 (1972) 173-174; Robinson, P. J., et al., Biotech Bioeng. (1973) 15, 603-606). The concept has been extended over time to include affinity purification of enzymes, proteins or microorganisms applicable to any sorption-desorption process (Dunhill, P., et al., Biotech. Bioeng. (1974) 10,987-990; Horisberger, M., Biotech. Bioeng. (1976) 18, 1647-1651).

Another improved magnetically responsive particle is described by Mansfield et al. in U.S. Pat. No. 4,197,337. These particles are porous glass microparticles with magnetic material imbedded within them. This gives the particles the properties of high surface area, inertness and being substantially superparamagnetic. This high surface area again favors rapid reaction kinetics and increases capacity of the individual particles. Being substantially superparamagnetic, basically means the particles do not retain much magnetic memory, or retentitivity, when removed from a magnetic field. This means that particles can be repeatedly separated from their environment by a magnetic field without affecting the ability to redisperse those particles. This is of advantage in sandwich immunoassays where multiple washing steps may require repeated separation and redispersion.

The protected $CrO_2$ particles described in the Du Pont patent have several properties that are particularly advantageous in heterogeneous immunoassays. These are:

low remanent magnetism and favorable surface structure—allowing repeated magnetic separation/dispersion cycles;

rapid separation in a magnetic field;

high surface area for high capture capacity;

a highly stable particle for maximum reagent shelf life.

One problem with immunoassays is that they require repeated washing of the solid support containing the bound component following removal of the free component. This is a particularly difficult procedure even when performed manually. It is a particular problem when the automatic wash procedure is incorporated into an automatic instrument which is capable of performing immunoassays. The typical requirements for purity in such immunoassays is that the bound component remaining following such washes should not contain more than 20 parts per million of the original sample/conjugate matrix. This necessitates the use of multiple wash stations and can be accomplished in automatic instruments by providing such multiple wash stations. However, the several mechanisms required to operate individually the several wash stations and the mechanisms required for the wash stations themselves can become quite expensive.

It is known in a conventional chemical analyzer an instrument produced by Hitachi, Inc., Tokyo, Japan, Model Number 7050 to link together or "gang" plural wash probes. When this is accomplished, however, the ability of the instrument to perform multiple analytical procedures at the same time or operation is severly impaired.

SUMMARY OF THE INVENTION

Many of these disadvantages to the prior art are overcome by using the apparatus and/or methods of this invention. This invention provides an improvement to an automatic analytical apparatus for performing immunoassays on samples using a solid support, the assays having bound and free phases, the bound phase being bound to the solid support, the apparatus adapted to receive a plurality of reaction vessels, and having a plurality of sequentially located processing positions, means to stepwise index the reaction vessels in sequence to the several processing positions for an analysis cycle, the index means effecting at least two such analysis cycles, the positions having means to add sample and/or reagents, to incubate, to wash, or to measure the contents of the vessels. According to this invention the wash means includes at least two wash probes coupled or ganged for simultaneous insertion into the reaction vessels at different processing positions. Further, the wash probes are positioned contiguous to the first one of the sample and/or reagent position in the sequence. The means for adding sample and/or reagents is disabled each cycle for a number of vessels leading and trailing the first and last vessels receiving sample or reagent, the number corresponding to the number of processing positions between the insertable wash probes.

The processing means are controlled according to different time-templates, each time-template controlling a different set of immunoassays to effect the first use of the wash means in the same cycle. The processing means time-template permit multiple assays to be performed simultaneously using different groups of reaction vessels. The index means may be a rotatable wheel or a continuous belt or chain type mechanism, each of which mechanisms is known in the prior art.

Using this apparatus the wash probes are not only ganged together, but separated into two groups to provide a high degree of versatility and lower cost wash mechanism and still achieve the goal of providing washed solid support which contains a minimal amount of the original serum/conjugate matrix such as used in heterogeneous immunoassays. The use of the gang wash apparatus can render it somewhat difficult to use multiple test protocols or procedures on the same batch of samples. This is alleviated by this invention by utilizing extra or "dummy" reaction vessels leading and trailing each group of test samples. The number of dummy vessels required is equal to two times the number of test positions between the first and last probe of the gang wash with the largest number of test positions between its first and last probes. In addition some test procedures require inter-woven dummy vessels in order to separate different test protocols that are being performed within the same batch. The number of interwoven dummy vessels is equal to the number of test positions between the first and last probes of the gang wash with the largest number of such test positions. Even these additional dummy vessels may be reduced appreciatively in number, according to this invention, by adjusting the test protocols to provide for the very first wash step of each step procedure to occur during the same apparatus cycle.

The method of this invention delays the starting time of specific protocols in a manner that causes all assays in the batch to require the first use of the wash means for each assay during the same cycle or revolution of the reaction wheel. The protocols for all assays have been developed so that subsequent use of the wash resource is also limited in a way that requires all assays still in progress to require a wash step during the same revolution of the reaction wheel. The vessels of assays which have been completed may be washed without harm during the processing of assays which have yet to complete.

The methods and apparatus of this invention permit many different tests or assays to be performed by a sequential, low cost analyzer which operates in a batch mode. This is true even though the several tests or assays have different reaction times before a wash and include a wash step as part of the assay.

BRIEF DESCRIPTION OF THE DRAWINGS

The invention may be more fully understood from the following detailed description thereof taken in connection with accompanying drawings which form a part of this application in which:

FIG. 2A is an enlarged view of the wand type bar-code reader and the reagent cartridge;

DETAILED DESCRIPTION OF THE PREFERRED EMBODIMENT

The preferred embodiment of this invention is described with particular reference to FIGS. 1-5 which depict the essential features of an automatic analytical apparatus that is capable of implementing the features of this invention. Many of the components of this automatic apparatus are, of course, well known in the art and hence will not be described in detail. However, the particular features of this invention including two separate gang wash units are described in detail. The dummy vessel features of the invention are implemented by software which will be described in conjunction with the flow charts of FIGS. 6A and 6B,. Also the time-templating features are software implemented and described in conjunction with the flow charts of FIGS. 6A and 6B.

The automatic apparatus described operates in a batch mode wherein all reagents and samples are set in the apparatus and all test requests are associated with each of those samples prior to the start of the batch. It is not generally possible to add a sample or test request once the batch has begun. This partial restriction is due to the plurality of process time-templates running concurrently which require that all assays run according to a particular time-template be initiated contiguously. This further requires that random access to samples be provided so that a sample which requires assays from more than one time-template can be accessed more than once with these accesses separated in time by access to other samples and/or reagents. This batch mode of operation is distinct from typical assembly line analyzers which process methods according to a single time-template and frequently allow a continuous or restricted flow of samples into the process stream after the batch has begun.

Figures 1, 6A:
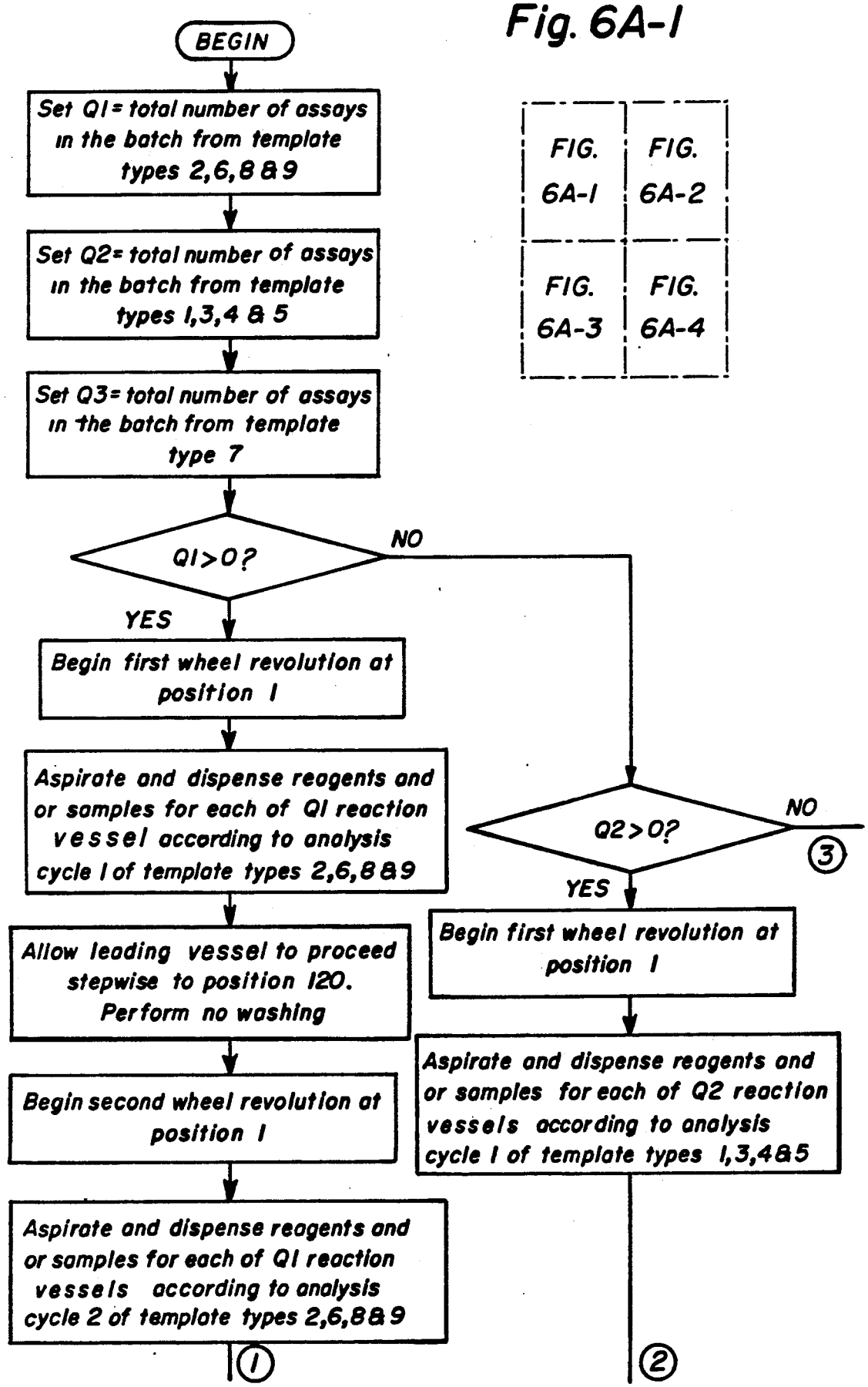
FIG. 1 is a perspective view of the apparatus of this invention.
FIGS. 6A and 6B are flow charts describing the software logic useful with the organization of protocols shown in Table 2.
Figures 2, 6A:
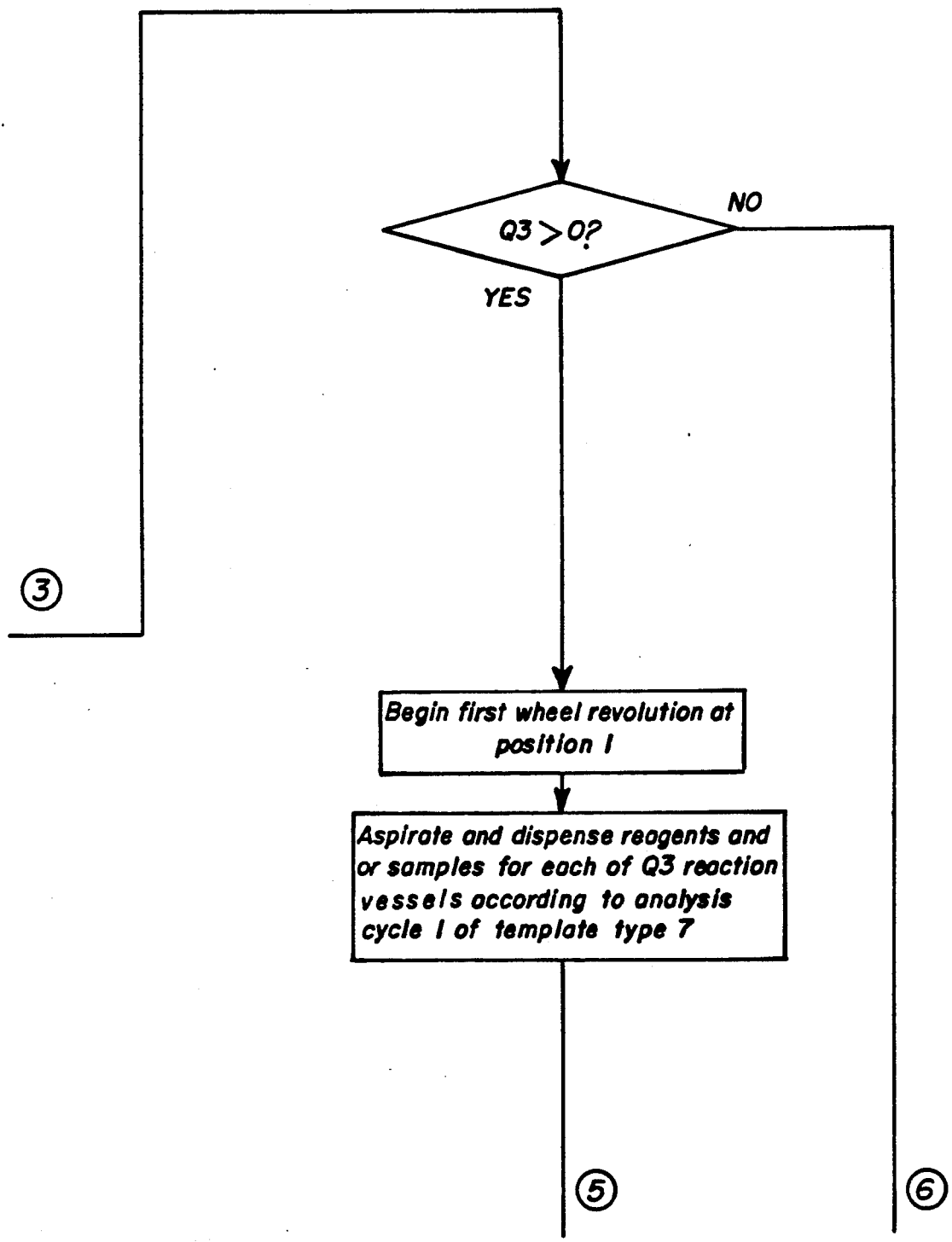
FIG. 2 is a pictorial view of the major components of the apparatus of FIG. 1.

With reference to FIG. 1, the preferred embodiment of the apparatus of this invention is composed of the following major elements to support the man-machine interface; a printer 10, CRT 12, and a keyboard 14. An area 16 is comprised of a guide slot and a fixed position bar code reader (FIG. 2) which together guide a reagent cartridge 52 (FIG. 2) as the operator pushes it and reads barcoded information on the side of the cartridge. Such information identifies the cartridge type. An area 18 is adapted to receive the reagent cartridge which is then pushed by the operator onto a reagent storage wheel (FIG. 2). Used reagent cartridges are also ejected from the instrument through this area 18. A floppy disk drive 20 operating with a central processing unit (CPU) housed in the apparatus and now shown is used to read in operating system software and to store system parameter changes and test results. A sample and reagent wheel 22 is used to support sample cups and special reagents. Vessels used to store reagents common to all assays are shown as 24, 26 and 32. Reaction vessels are grouped in clusters 30 and placed on a reaction wheel (not shown in FIG. 1). A lid 34 covers various thermally controlled areas during operation and a second lid 36 isolates all fluids and mechanical motion from the laboratory environment during operation.

FIG. 2 illustrates the major rotating components of the preferred embodiment of the automatic apparatus of FIG. 1. A reagent wheel 44 is adapted to receive a plurality of reagent cartridges 52. A sample wheel 22 preferably positioned coaxially within the annular configured reagent wheel 44 receives a plurality of samples, standards and special reagents held in sample cups 23. Both the sample wheel 22 and the reagent wheel 44 rotate bidirectionally on the same shaft 48. The sample wheel 22 may be separated from the reagent wheel 44 and may be removed from the apparatus for loading and cleaning. The reagent wheel 44 is cooled, the sample wheel 22 is not. Each reagent cartridge 52 has a barcode label (not shown) which is read by a wand type barcode reader 16. The information on the label may also be entered via the keyboard 14 in lieu of the barcode reader mechanism. Each reagent cartridge 52 preferably is a multi-compartmented container such as those sold under the tradename FLEX TM by E. I. du Pont de Nemours and Co., Inc., Wilmington, Del., USA. Desirably the cartridge should be capable of being shaken if it contains one or more reagents in suspension, or at least one of its compartments 51 should be vortexable. To permit this, the compartment 51 should be flexibly mounted at its top such that its bottom may be nutated. The flexible mounting may be accomplished by connecting the compartment 51 by a "living" hinge to cartridge 52. Clusters 30 of reaction vessels 66 (FIGS. 2 and 4) are arrayed about a reaction wheel 58 which rotates in a clockwise fashion about a drive shaft 62. Preferably, the reaction wheel is rotated in a stepwise fashion to sequentially move each reaction vessel step by step through a complete cycle (360° rotation). The number of reaction vessels in a cluster 30 typically may be 10 and the number of clusters 30 on the reaction wheel 58 may be 12. These quantities can vary in applications where mechanical resources must have different timing or index cycles due to chemistry requirements or hardware limitations.

A fluorometer 64 is so disposed as to make one or more measurements of the fluorescence intensity at one or more wavelengths from a single reaction vessel 66 with each index or step of the reaction wheel 58. The excitation light flux is at a 90 degree angle to the emitted light flux which exits the reaction vessel 66 through the bottom and enters a photomultiplier (not shown). A pipetting device 28 transfers fluid from either sample cups 23, reagent cartridges 52, generic reagent container 24 or generic reagent container 26 to a reaction vessel 66. The pipette probe (not shown) is cleaned between each use at a rinsing drain resource 70. A wash resource 76 which aspirates fluid from reaction vessels 66 via a peristaltic pump 78, dispenses a wash buffer into reaction vessels 66 and separates magnetic particles from the fluid in the reaction vessels 66 is shown in more detail in FIG. 4.

Figures 3, 6A:
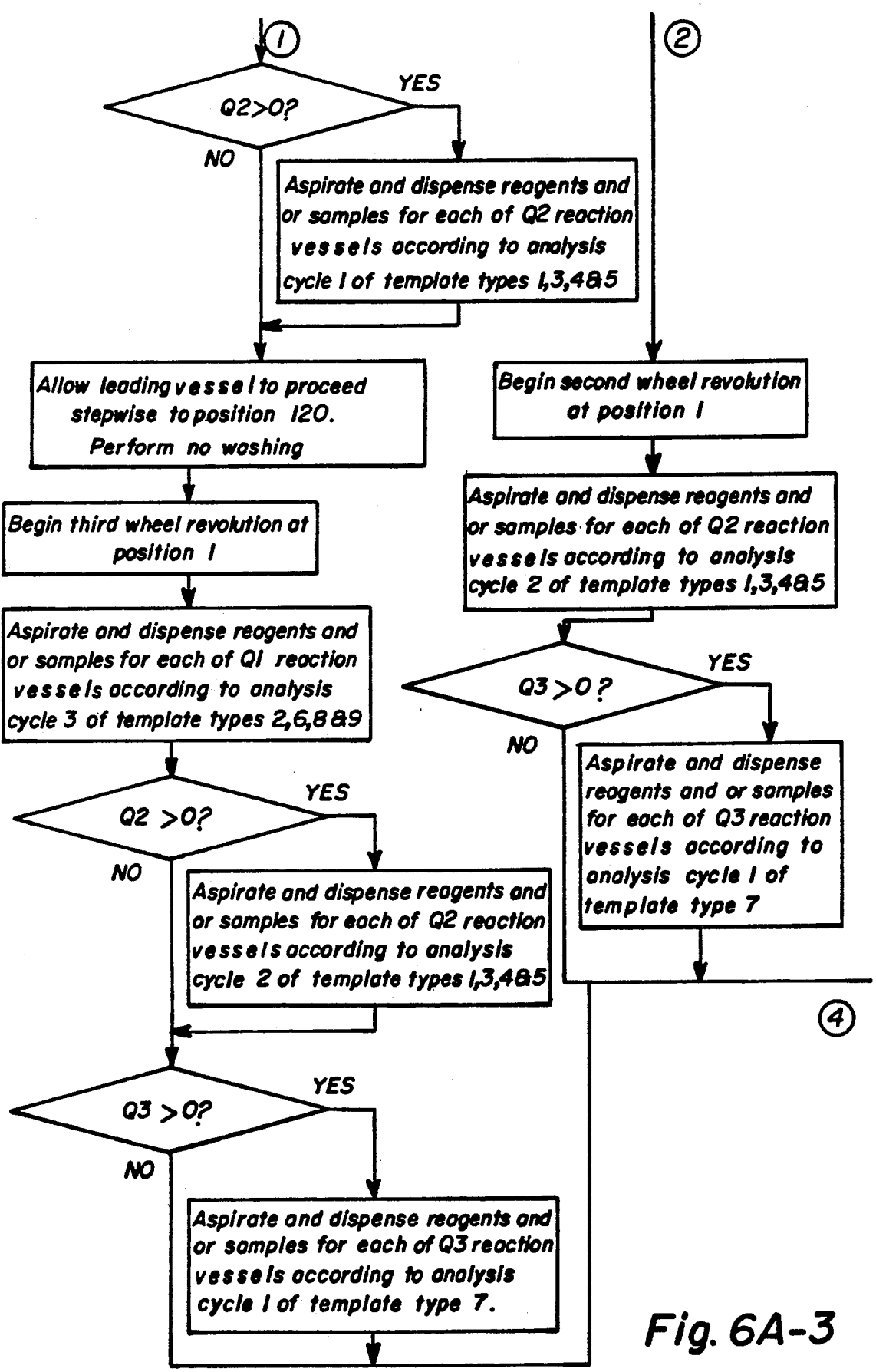
FIG. 3 is a diagrammatic plan view of the top of the apparatus of FIG. 1.
Figures 4, 6A:
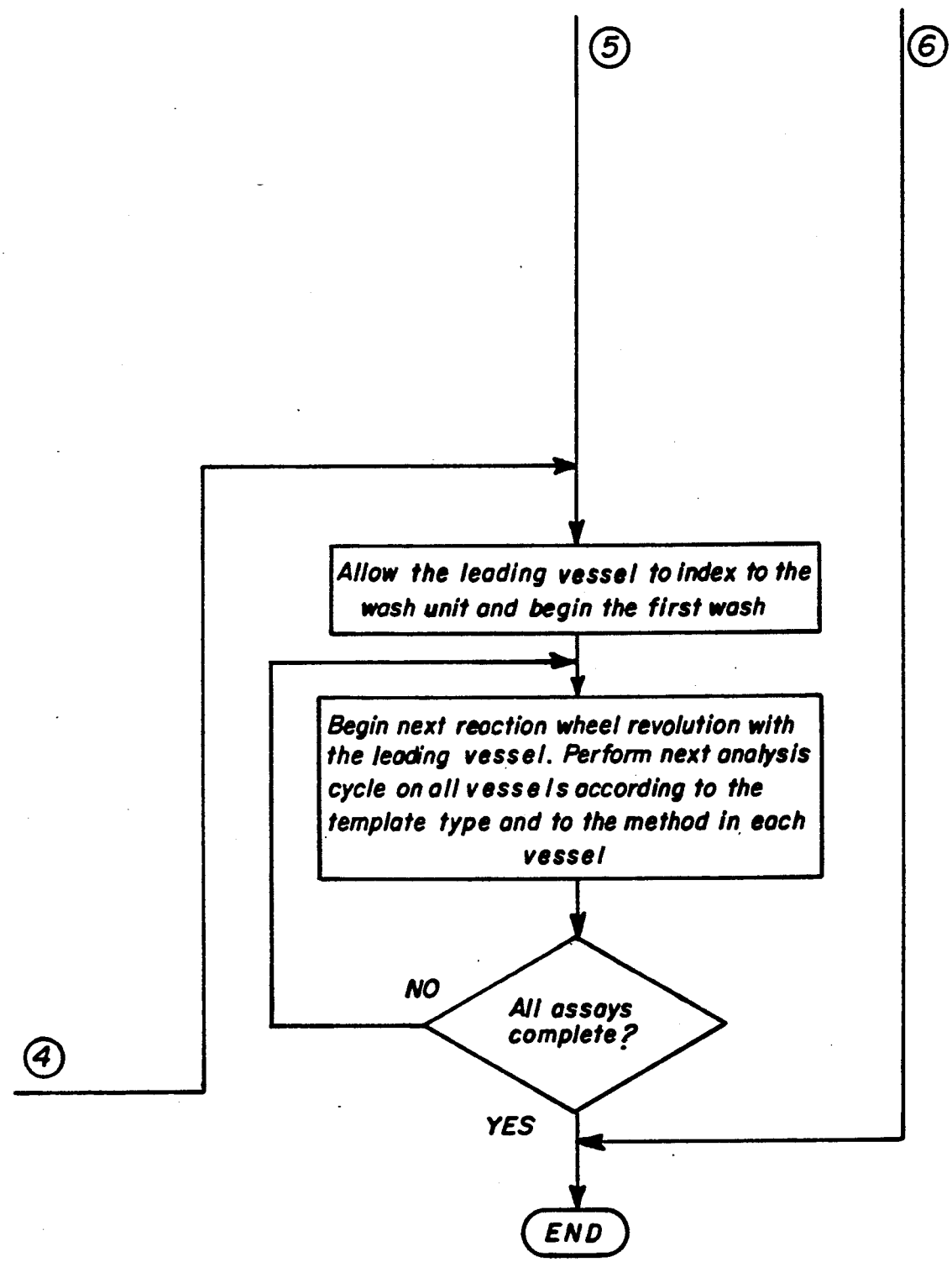

FIG. 3 illustrates the three wheels 22, 44 and 58 and the pipetting mechanism 28 motion in more detail. Reagent wheel 44 and sample wheel 22 rotate bidirectionally about shaft 48. A plurality of sample cups 23 are arrayed about the sample wheel 22 in two concentric groups. The pipetting device 28 pivots about a shaft 105 so that movement of the pipetting probe tip (not shown) describes an arc 106 intersecting all three wheels giving the probe tip access to the following dispense and or aspirate locations: reagent and/or sample dispense into a reaction vessel 108, probe discharge and wash 110 at the rinsing drain resource 20, reaction buffer aspirate 112 from generic reagent container 26, reaction substrate aspirate 116 from generic reagent container 118, six reagent aspirate positions 122, where position 123 is unique in that mixing is provided for the reagent in the well or compartment 51 under that position by a vortexing device (not shown), and two sample positions 124. Shaft 48 rotates both the sample wheel 22 and the reagent wheel 44 simultaneously in order to bring the required reagent well or sample cup 23 under the probe tip which may be located at any of positions 122 or 124 as required by the assay protocol. Reaction wheel 58 is rotated clockwise by drive shaft 62 and supports a plurality of clusters 30 of reaction vessels 66. In an exemplary embodiment, as will be used in describing this invention, there are twelve clusters 30 of ten vessels 30 in each cluster for a total of one hundred twenty reaction vessels 66. The reaction wheel 58 and its contents are thermally controlled at 37° C.

The wash resource 76 performs several functions. It (a) dispenses wash buffer into reaction vessels at processing positions 138, 146 and 154; (b) aspirates fluid from reaction vessels at processing positions 144, 152, 160 and 162; (c) resuspends or mixes the contents of the reaction vessels at processing positions 138, 140, 146, 148, 154, and 156; (d) separates the bound and free phases at processing positions 142, 150 and 158 in order for the wash process to proceed and at processing positions 132 in order for the fluorometric process to proceed at processing position 134. Whenever the term "wash" is used in the claims, it should be considered as potentially including one or more of these four functions. As will be described, the wash resource 76 is divided into two parts 208 and 212, each of which operate independently of each other.

The basic incubation area extends from processing positions 108 to 136 yielding a thirty minute incubation for each reaction vessel which in an exemplary case is indexed three degrees every eighteen seconds. A shorter incubation period is provided between processing positions 108 and 164 for color or fluorophor development while a longer incubation period of thirty-six minutes is possible, beginning at processing position 108 and ends at the immediately preceding processing position if the wash resource 76 is not activated to remove any reactants during that period.

Figure 4:
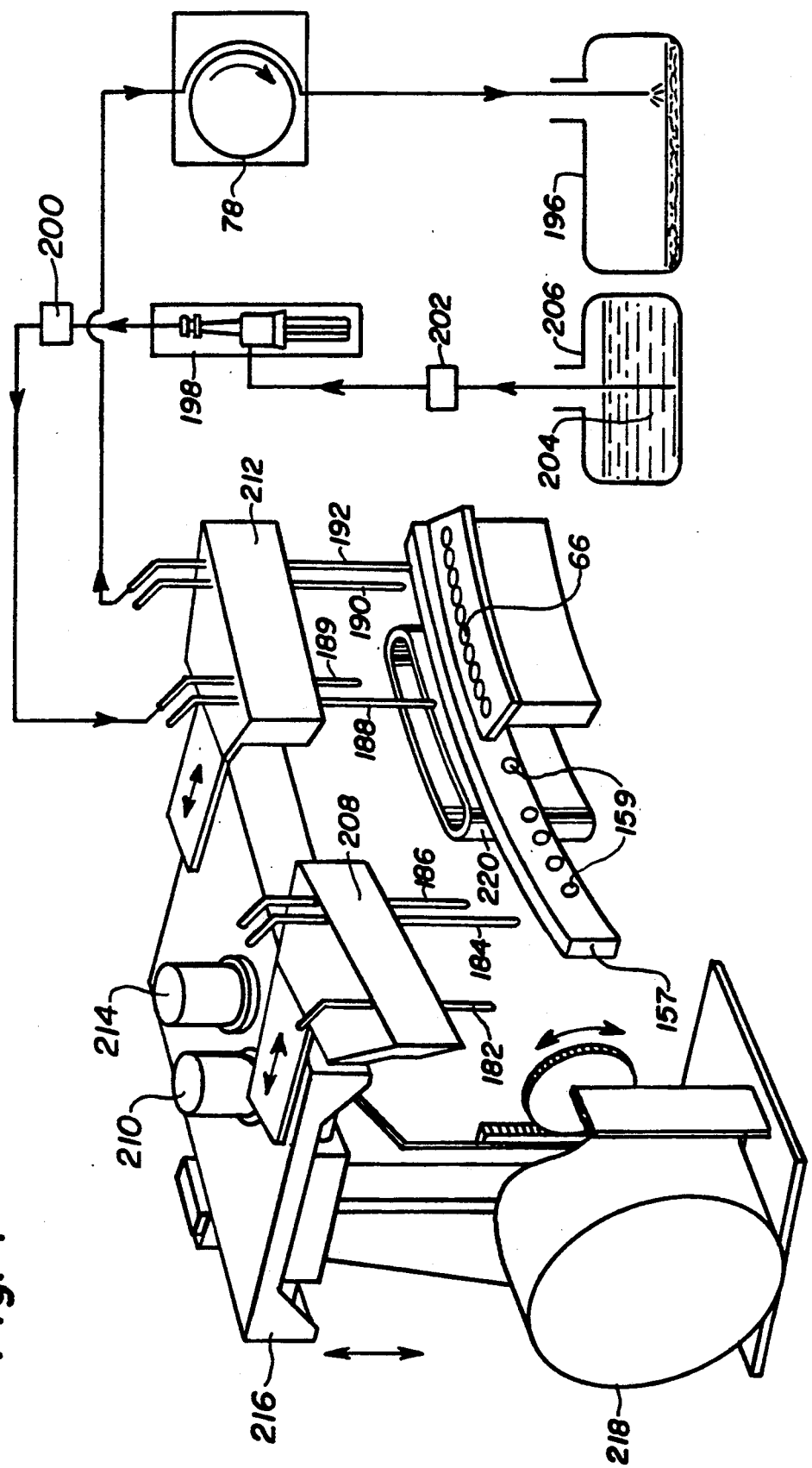
FIG. 4 is a pictorial view of the wash module major components used in the apparatus of FIG. 1.

FIG. 4 illustrates the basic mechanisms, magnetic separation and fluids associated with the wash resource 76. The fluidics part of the wash resource removes liquids from and dispenses wash buffer into the reaction vessels 66 as they rotate below the probes 182 through 192, corresponding to processing positions 138, 144, 146, 152, 154, 60 and 162 respectively. Probes 182, 186 and 189 dispense wash buffer 204 obtained from container 206 via a pump mechanism consisting of a two port syringe 198 and valve assemblies 200 and 202. These probes are fixed in relative position within a first block 208 which is moved back and forth via motor 210. Probes 184, 188, 190 and 192 aspirate fluid from reaction vessels via peristaltic pump 194 which delivers said fluid to waste container 196. These probes are fixed in relative position within a second block 212 which is moved back and forth via motor 214. Both of these probe group mechanisms are held by a platform 216 which is moved up and down by motor 218. These motors allow probes to be completely up or completely down in either the reaction vessels or in a drain cup 220. Furthermore, the left group of probes can be in the drain cup 220 while the right group of probes is in reaction vessels or vice versa. This grouping of the probes within a block is often referred to as gang wash. An example of a multiple or gang wash type mechanism is described in U.S. Pat. No. 4,451,433 assigned to Hitachi, Ltd., and in Hitachi Model 7050 analyzer.

As mentioned previously the preferred embodiment of this invention uses magnetic particles as a solid support. Alternatively, of course, beads or the tube walls may be coated and used as a solid support utilizing known procedures. In these cases, the reaction vessels would have to be preloaded in known positions with coatings or beadss for the particular assay to be carried out. In the preferred embodiment, however, where magnetic particles are used as the solid support, the solid support must be separated from the liquid contents of each reaction vessel. This is accomplished by placing permanent magnets 159 with either the south or north pole in the face of a non-ferromagnetic frame 222. Thus the magnet positions are located at 157 in the face of the frame 222. The location of these permanent magnets is at the processing positions illustrated in FIG. 3 where separations occurs and represented by the numerals 142, 150 and 158. The application, filed by Lee and Davis, Ser. No. 230,449 describes an improved separating mechanism and is incorporated herein by reference.

Similarly, mixing or resuspension of the magnetic particles at processing positions 138, 140, 146, 148, 154 and 156 is accomplished by causing a vortex to form in the vessels as is the usual practice done in the manipulation of samples in chemical laboratories. Devices are available for this purpose and comprise a disc which is eccentrically rotating. The disc is moved into contact with the bottom of the vessel or not as mixing is required. If particles that settle are used, all reaction vessels 66 are subjected to a mixing action during each step of the reaction wheel. Preferably balls having a low magnetic retentivity may be used and the reaction wheel cycled back and forth or vibrated each step so that the balls do the mixing by placing such a ball in each reaction vessel. Since neither the separation nor the mixing functions are a feature of this invention they will not be described further, but rather the subject matter of these copending applications is incorporated herein by reference.

Figure 5:
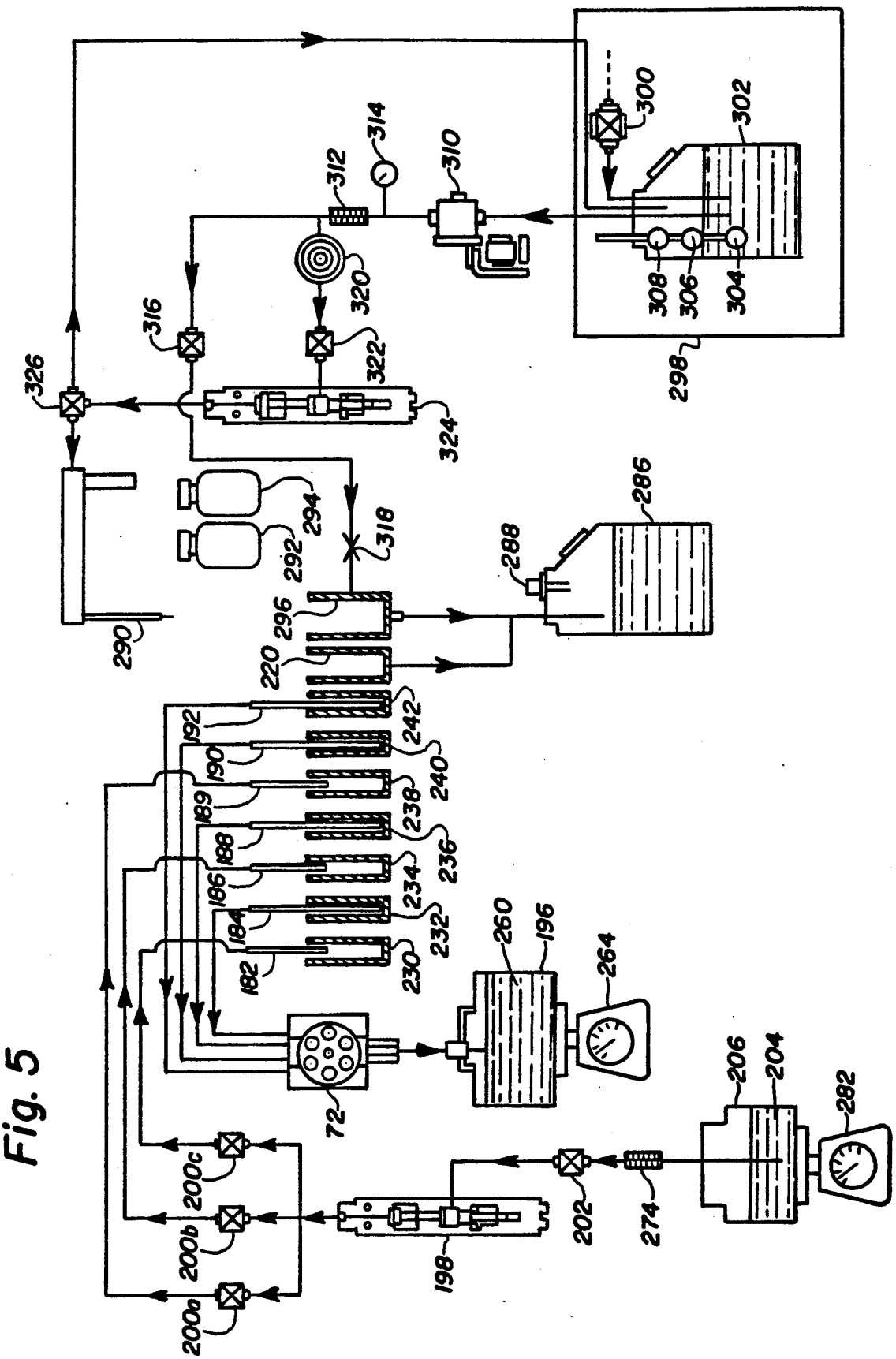
FIG. 5 is a fluidic diagram of the apparatus of FIG. 1.

FIG. 5 illustrates the fluidics of the preferred instrument. Reaction vessels 230 through 242 are moved sequentially under each of probes 182 through 192. These reaction vessels although arranged and moved in the order illustrated are not necessarily adjacent, but rather are separated by a number of other vessels depending upon the operations such as resuspension, incubation and separation required between probe positions as illustrated in FIG. 4. Probes 184, 188, 190 and 192 are connected by four fluid lines to peristaltic pump 78 which moves waste fluid 260 from vessels 232, 236, 240 and 242 respectively to the waste container 262. The volume contained in waste container 196 is monitored by a weight sensor 264 in order to avoid overflow situations. Weight sensor 282 monitors the volume of wash buffer 204 remaining in container 206. This wash buffer is aspirated by a pump consisting of a dual port syringe 198 and valves 202, 200a, 200b and 200c through a filter 274. By controlling the state of these valves, different volumes of wash buffer may then be dispensed at different times though each of the dispense probes 182, 186 and 189. As shown in FIG. 4 a drain cup 220 is so arranged as to receive any priming fluid or drippage from all the probes and conduct that fluid to the waste container 286. Conductivity sensor 288 protects the waste fluid from overflowing this container.

Deionized water or a suitable buffer is provided to the instrument through the items contained in block 298 which are all located external to the instrument although controlled by the instrument. Valve 300 admits deionized water to storage container 302. Float sensors 304, 306, and 308 detect low fluid levels, full fluid level and overflow conditions. Diaphragm pump 310 removes deionized water from the container 302 which is then filtered by 312. Pressure gauge 314 detects blockage in the fluid lines. Water is recirculated to container 302 though degasser 320, valve 322, two port syringe 324 and valve 326. Recirculation may be stopped by switching valve 326 whereupon the probe 290 may be copiously rinsed in the inside. If valve 322 is closed and valve 326 is open in the direction of the probe 290, then the syringe can be used to accurately and precisely aspirate fluids from reagent containers or sample cups and to also accurately and precisely dispense them into reaction vessels along with a water chase Valve 316 allows the liquid to flow through a flow restrictor and into the drain 296 where it rinses the outside of the pipette mechanism probe 290.

OPERATION

Table 1 and Table 2 describe nine of the many possible analytical or time-templates suitable for use with the apparatus of this invention with Table 1 describing a typical multiple time-template organization and Table 2 describing an alternative templating scheme. A time-template is the procedure, program or process stored, e.g., on a floppy disc, which controls through the CPU the operations of the several resources, the reaction, sample, and reagent wheels to effect the several assays. These assays, described by the several time-templates, require several revolutions or cycles of the reaction wheel 58. In describing the several different analytical procedures or assays, the preferred heterogeneous assays using magnetic particles are described. Both tables relate time-template types to each of up to seven revolutions of the reaction wheel.

TABLE 1

| ANALYSIS TEMPLATE | REVOLUTION ONE | | | | | REVOLUTION TWO | | | | | REVOLUTION THREE | | | | | REVOLUTION FOUR | | | | | REVOLUTION FIVE | | | | | REVOLUTION SIX | | | | |
|---|---|---|---|---|---|---|---|---|---|---|---|---|---|---|---|---|---|---|---|---|---|---|---|---|---|---|---|---|---|---|
| | CYCLE | FLUID 1 | FLUID 2 | INCUBATE | WASH | CYCLE | FLUID 1 | FLUID 2 | INCUBATE | WASH | CYCLE | FLUID 1 | FLUID 2 | INCUBATE | WASH | CYCLE | FLUID 1 | FLUID 2 | INCUBATE | WASH | CYCLE | FLUID 1 | FLUID 2 | INCUBATE | WASH | CYCLE | FLUID 1 | FLUID 2 | INCUBATE | WASH |
| 1 | 1 | — | S | 36 | NO | 2 | R 1 | R 2 | 30 | YES | 3 | buf | sub | 4 | XX | | | | | | | | | | | | | | | |
| 2 | 1 | S | | 36 | NO | 2 | R 1 | R 2 | 36 | NO | 3 | R 3 | R 4 | 30 | YES | 4 | buf | sub | 4/M | XX | | | | | | | | | | |
| 3 | 1 | R 1 | R 2 | 36 | NO | 2 | — | S | 30 | YES | 3 | R 3 | R 4 | 30 | YES | 4 | buf | sub | 4/M | XX | | | | | | | | | | |
| 4 | 1 | — | S | 36 | NO | 2 | R 1 | R 2 | 30 | YES | 3 | R 3 | R 4 | 30 | YES | 4 | buf | sub | 4/M | XX | | | | | | | | | | |
| 5 | 1 | — | S | 36 | NO | 2 | R 1 | R 2 | 30 | YES | 3 | R 3 | R 4 | 30 | YES | 4 | R 5 | R 6 | 30 | YES | 5 | buf | sub | 4/M | XX | | | | | |
| 6 | 1 | — | S | 36 | NO | 2 | R 1 | R 2 | 36 | NO | 3 | R 3 | R 4 | 30 | YES | 4 | R 5 | R 6 | 30 | YES | 5 | R 7 | R 8 | 30 | YES | 6 | buf | sub | 4/M | XX |
| 7 | 1 | R 1 | R 2 | 30 | YES | 2 | S | — | 30 | YES | 3 | S | — | 30 | YES | 4 | R 5 | R 6 | 30 | YES | 5 | buf | sub | 4/M | XX | | | | | |
| 8 | 1 | R 1 | R 2 | 36 | NO | 2 | — | R 3/4 | 36 | NO | 3 | R 1 | R 2 | 30 | YES | 4 | R 3 | R 4 | 30 | YES | 5 | R 5 | R 6 | 30 | YES | 6 | buf | sub | 4/M | XX |
| 9 | 1 | — | S | 36 | NO | 2 | R 1 | R 2 | 36 | NO | 3 | — | — | 30 | YES | 4 | buf | sub | 4/M | XX | | | | | | | | | | |

TABLE 2

| Analysis Template | Revolution One (Cycle / Fluid 1 / Fluid 2 / Incubate / Wash) | Revolution Two | Revolution Three | Revolution Four | Revolution Five | Revolution Six | Revolution Seven |
|---|---|---|---|---|---|---|---|
| 1 | 1 / — / S / 36 / NO | 1 / — / S / 36 / NO | 2 / R 1 / R 2 / 30 / YES | 3 / buf / sub / 4 M / XX | | | |
| 2 | | 2 / R 1 / R 2 / 36 / NO | 3 / R 3 / R 4 / 30 / YES | 4 / buf / sub / 4 M / XX | | | |
| 3 | | 1 / R 1 / R 2 / 36 / NO | 2 / — / S / 30 / YES | 3 / R 3 / R 4 / 30 / YES | 4 / buf / sub / 4 M / XX | | |
| 4 | | 1 / — / S / 36 / NO | 2 / R 1 / R 2 / 30 / YES | 3 / R 3 / R 4 / 30 / YES | 4 / buf / sub / 4 M / XX | | |
| 5 | 1 / — / S / 36 / NO | 1 / — / S / 36 / NO | 2 / R 1 / R 2 / 30 / YES | 3 / R 3 / R 4 / 30 / YES | 4 / R 5 / R 6 / 30 / YES | 5 / buf / sub / 4 M / XX | |
| 6 | | 2 / R 1 / R 2 / 36 / NO | 3 / R 3 / R 4 / 30 / YES | 4 / R 5 / R 6 / 30 / YES | 5 / R 7 / R 8 / 30 / YES | 6 / buf / sub / 4 M / XX | |
| 7 | 1 / R 1 / R 2 / 36 / NO | 2 / R 1 / R 2 / 36 / NO | 3 / R 3 / R 4 / 30 / YES | 4 / R 3 / R 4 / 30 / YES | 4 / R 5 / R 6 / 30 / YES | 4 / R 5 / R 6 / 30 / YES | 5 / buf / sub / 4 M / XX |
| 8 | 1 / — / S / 36 / NO | 2 / — / S / 36 / NO | 3 / R 1 / R 2 / 30 / YES | 4 / buf / sub / 4 M / XX | 5 / — / S / 30 / YES | 6 / buf / sub / 4 M / XX | |
| 9 | | 2 / R 1 / R 2 / 36 / NO | 3 / — / S / 30 / YES | 4 / buf / sub / 4 M / XX | | | |

Each revolution of the reaction wheel 58 is further described with an analysis cycle number; a fluid 1 and-/or a fluid 2 type to be dispensed into each reaction vessel where (—) is no fluid, (S) is sample, (R1) through (R8) are reagent types from the reagent cartridges, (buf) is substrate buffer, (sub) is tag-enzyme substrate, the incubation period is given in minutes (30), (36) or (4M) and the use of the wash resource during that revolution is either (NO), (YES) or (XX). (4M) in the incubate column indicates a 4 minute incubation followed by a fluorescent measurement. (XX) in the wash column indicates both that no wash is required by that time-template and that if a wash is required by another coprocessing time-template then the assays in the former time-template will not be affected by any wash step being carried out by the latter time-template.

A typical use of time-template type 1 is for the measurement of hormones such as thyroid stimulating hormone (TSH) or for cancer markers such as alpha-feto protein (AFP). In this time-template sample(s) is added during the first cycle or revolution of the reaction wheel 58 to the desired reaction vessels 66. In the second revolution, magnetic particles coated with antibodies specific to the analyte of choice (TSH or AFP, etc.) and antibody enzyme conjugate are immediately added to the sample by the pipetting device 28. The antibody in the antibody enzyme conjugate is also specific to the same hormone or marker as the antibody on the magnetic particles. In the case of the preferred apparatus, the enzyme alkaline phosphatase (ALKP) is coupled to the antibody to form the conjugate. Thus during the incubation phase of the second revolution, a sandwich is formed consisting of the solid support (magnetic particles) coupled to the analyte of interest (e.g. TSH or AFP) which is coupled to the conjugate bearing an active enzyme (ALKP). The last step of revolution two of the reaction wheel effects a wash, i.e., it separates the magnetic particles by the action of the magnets 157 and hence all of the molecular "sandwiches" from the free or liquid phase of the reaction. The liquid phase is removed, i.e., aspirated, by the wash resource 76 thus removing excess unreacted conjugate and sample together with nearly all the possible chemical interferences from the sample. The wash resource 76 then resuspends the magnetic particles by dispensing a wash buffer and mixing the contents of the reaction vessel. In order to more completely wash the magnetic particles, the processes of separation, aspiration and resuspension is repeated. For the same reasons as the first two wash steps the separation of magnetic particles is carried out a third time at processing positions 158 and the free phase fluid is removed again with aspiration occurring at two processing positions 160 and 162 in order to assure precise removal of free phase fluid.

At this point revolution three begins with the addition of substrate buffer and substrate, which substrate in the preferred apparatus is 4-methylumbiliferone phosphate (MUP). During the subsequent short incubation period of four minutes ending at the processing position 164, enzyme (ALKP) coupled to the magnetic particles during the previous incubation step cleaves the phosphate from the MUP, converting the MUP to 4-methylumbiliferone (MUB), at a rate related directly to concentration of the analyte in the original sample. The magnetic particles are separated again at processing positions 132 and when they are completely separated, the fluoresence of MUB, which fluoresces at a distinctly different wavelength than MUP, is measured and subsequently converted to an analyte concentration via a mathematical relationship determined via the use of calibrators.

A typical use of time-template 2 is for the measurement of haptens such as thyroxine (T4). In the T4 assay, sample is added during the first revolution of time-template type 2. Since the sample volume tends to be small, the pipetting system chases the sample in each reaction vessel with a volume of deionized water sufficient to avoid any deletrious effects of sample evaporation. During the second revolution a single releasing reagent is added (even though two are permitted by the time-template type 2) and allowed to incubate thus making all protein bound T4 available to the next capture steps. Although the reagents added in the third revolution include magnetic particles and an enzyme conjugate, the chemistry is considerably different than that of the TSH assay. The instrument processing of fluids, however, is the same as for revolution 2 of time-template 1. The fourth revolution of time-template 2 proceeds in the same fashion as the third revolution of time-template 1.

DUMMY VESSELS

According to one aspect of this invention, as previously described, the gang washes are split into separate blocks 208 and 212 for reasons that will now become apparent. Assume now that all samples and reagents are set and all test requests have been made and that the reaction wheel is loaded with one hundred tests all requested from methods represented by analysis time-template 1 as shown in Table 1.

During the first 30 minutes, 100 samples would be aspirated from sample cups 23 and dispensed at 18 second intervals to each of 100 reaction vessels 66. During the next 6 minutes the first twenty samples will have entered the wash resource 76 but no wash will have been performed, thus each sample will be incubated for 36 minutes by the end of the first wheel revolution. During the first 30 minutes of the second revolution one or two reagents are aspirated from reagent cartridge 52 and dispensed to each of the 100 samples with reagent type or types and quantities determined by each specific method using this time-template. When the leading vessel arrives at position 138 the wash process begins.

Consider the operation of the wash station with reference to both FIGS. 3 and 4. When the leading vessel in an assay is ready to be washed and that cup reaches position 138, then probes 182, 184 and 186 from the block 208 above positions 138, 144 and 146 respectively are caused to enter vessels simultaneously and aspirate or dispense simultaneously. In order to prevent aspiration of fluid from or contamination of a reaction vessel for other assays, six empty or dummy reaction vessels 66 are located (simply by not filling them with reagent or sample) ahead of the leading reaction vessel. This permits the aspiration or dispensing which occurs by the probes in the first block 208 to take place harmlessly in empty vessels 66. Furthermore, when the leading reaction vessel reaches position 152 then a total of seven dummy vessels are in fact required as probes 188, 189, 190 and 192 are lowered into vessels at positions 152, 154, 160 and 162 respectively. It is readily seen that if the wash resource were not split into two separately controlled probe groups 208 or 212 that eighteen dummy vessels would be required as the leading vessel began the wash process at position 138 and all probes were lowered into reaction vessels through position 162. In all cases, the minimum number of dummy vessels is set at one more than the maximum number of vessels between the first and last probe of the probe group simultaneously entering the reaction vessels. It is thus seen that the features of having the two separate sections of the gang wash resources, as depicted in blocks 208 and 212 of FIG. 4, is an economical manner in which to implement the requirements for high purity of the solid support in the heterogeneous immunoassays. Also, individual mechanisms are not required for each of the several wash probes 182, 186 and 189 and the several aspirate probes 184, 188, and 190 and 192.

Continuing on with operation of time-template 1, when the leading reaction vessel arrives at dispensing position 108, revolution three of the time-template begins. During the next 30 minutes substrate buffer and substrate is added to each of the 100 vessels as each reaches position 108. The reactants are allowed to incubate until position 134 is reached and a fluorescence measurement is made, the final concentration of the analyte in question then being computed and made available. When the trailing (100th) vessel reaches position 162 it will be followed by; seven additional dummy vessels created by the action of probes 188, 190 and 192 entering the vessels; six unused vessels; and the seven dummy vessels which were in front of the leading vessel. Thus fourteen dummy vessels are created for all batch sizes in the range of 1 to 100 assays for a single analytical time-template type.

The use of the dummy vessels permits multiple tests to be run simultaneously in a sequential type machine in which all reaction vessels use the same resources more than once. On the other hand, the required number of dummy vessels is one more than the number of vessels between the first and last probe of a probe group that simultaneously enters the reaction vessels. If all of the aspirate and wash probes have been placed on a single block, a total of 20 dummy vessels would be required rather than the 14 as is required in order to permit multiple immunoassays to be run on the same machine batch. It is clear that a single gang wash requires 18 dummy vessels at the beginning and end of the assays being run. In a batch of 100 assays on a reaction wheel with 120 vessels, 16 of the trailing dummy vessels would overlap 16 of the leading dummy vessels groups of dummy vessels resulting in a total of 20 dummy vessels. If the number of assays in a batch was sufficiently reduced, the amount of overlap would decrease to a point where the maximum number of dummy vessels is 36 in the single block design. It is a further advantage of the split gang wash design that the number of dummy vessels is never more than 14. The use of the dummy vessels in and of itself is unique in that it does facilitate such multiple test operation. A further advantage of the split gang wash over a single gang wash incorporating all probes is the availability for analytical use of the vessels, located between the last probe of the first gang wash and the first probe of the second gang wash. These vessels, which would have been dummy vessels had the gang wash not been split, can now be used for assays, optical blanks, photometric standards calibrators or cleaning solutions.

Suppose that test requests were then made for a new batch which includes 50 assays of time-template type 1 and 50 assays of time-template type 3 from, both from Table 1. During the first 15 minutes of revolution one 50 samples (S) of the time-template 1 methods would be dispensed. During the next 15 minutes reagents (R1) and (R2) for each of the 50 time-template 3 assays would be dispensed. No wash would be carried out in the next 6 minutes. During the first 15 minutes of revolution two of the reaction wheel, reagents (R1) and (R2) for each of the 50 time-template 1 assays would be dispensed. During the next 15 minutes 50 samples (S) of the time-template 3 methods would be dispensed. The first wash would then begin on the next wheel index step and washing would continue for the next 99 indexes since both time-template types call for a wash during this second revolution. When the leading sample reaches processing position 108, revolution 3 begins and buffer and substrate are dispensed into each of the 50 time-template 1 vessels. When each vessel of time-template type 1 indexes past processing position 134, the assay being performed in that vessel is considered complete. When the leading vessel of time-template type 3 reaches position 108 and for the next 15 minutes, reagents (R3) and (R4) are dispensed in each of the 50 time-template 3 vessels. When the leading cup of time-template type 3 reaches position 138 and the second wash begins, six leading dummies are created in the block of time-template 1 vessels. This is not a problem since all time-template 1 assays have been completed and only useless reactants are being aspirated. Washing of time-template 3 vessels continues and revolution 4 begins and ends with the 51st and 100th vessel respectively. This batch still requires 7 leading and 7 trailing dummy vessels for a total of fourteen. The dummy vessels at the end of time-template type 1 have served two functions and are not considered to be actual dummies.

It is thus seen from Table 1, analytical time-template types 1, 3, 4 and 5 may be run conveniently in the same batch. The reasons this is so are that the first use of the wash resource coincides for each time-template and each subsequent use of the wash resource with split blocks coincides or does not matter. Furthermore, the time-template types may be run in any order. It is also possible to run assays completely randomly within this time-template group. The preferred embodiments for this mode of operation group all assays of the same type consecutively on the reaction wheel (for example, all TSH reaction vessels are contiguous, followed by all AFP reaction vessels, etc. This minimizes reagent to reagent carryover between methods. Alternatively, group all assays from the same sample together in order to minimize sample to sample carryover. For example, TSH and AFP reaction vessels for sample 1 followed by TSH and AFP reaction vessels for sample 2. It is also recognized for the same reasons, that all assays from analytical time-templates 2, 6, 8 and 9 may be similarly run in the same batch, i.e., the first wash occurs in the third revolution of the reaction wheel. It is not possible to combine assays from these to groups of time-templates nor is it possible to combine analytical time-template type 7 with any other time-template because the first use of the wash resource does not coincide between time-template groups.

INTERDUMMY VESSELS

An example of one means to combine all assays from the Table 1 analytical time-templates is now described. Assume that 86 test requests have been made representing 6 requests from time-template type 9 and 10 requests for tests from each of the other 8 time-templates. During the first 3 minutes of revolution 1, dispense the first two reagents (R1) and (R2) for each of the 10 time-template type 7 methods. During the next 136 seconds, create 7 "inter-dummy" vessels by dispensing nothing. During the next 12 minutes dispense the samples and or reagents required by the 40 samples in time-template types 1, 3, 4, and 5 starting with the 18th reaction vessel. During the next 136 seconds, create 7 more "inter-dummy" vessels by dispensing nothing starting with the 59th reaction vessel. Starting with the 65th vessel, dispense the samples and or reagents of the remaining 36 assays from time-template types 2, 6, 8, and 9. At this point 30 minutes have elapsed, 86 assays have been started and 14 "inter-dummies" have been created, which vessels will not be used by any assay.

When the leading vessel then indexes into position 138, the first wash begins on the time-template type 7 methods which creates the usual 7 leading dummy vessels bring the total number of dummy vessels up to 21. When the tenth vessel reaches position 162 the first group of "inter-dummy" vessels will have come into play by protecting assays of time-template types 1, 3, 4 and 5 from the effects of the wash resources since those and all the remaining assays on the reaction wheel do not require a wash during the first revolution. A similar process occurs during the second revolution where each of the 86 assays has the appropriate sample or reagent added and the second wash is begun on time-template type 7 assays, the first wash is begun on time-template types 1, 3, 4, and 5 assays, but no wash is begun on the vessel of time-template type 2, 6, 8 or 9 assays which are protected by the second group of "inter-dummy" vessels. By the end of the third revolution for the 100th reaction vessel, 7 more standard dummy vessels have been created after the time-template type 2, 6, 8, and 9 methods. The total number of dummy vessels stands and remains at 28. All assays complete in the same manner as the two time-template example described above. This combination of time-template types in a single batch or test run is possible because of the use of dummy vessels, 14 created as 7 leading and 7 trailing vessels by allowing the wash resource to operate on the, the balance created by not using them at all.

ADJUST TIME-TEMPLATE START TO PROVIDE STANDARD WASH CYCLE

In accordance with still another embodiment of this invention, the various analytical assays may be run in the same batch by running the several assays according to different time-templates such that the first wash of each assay occurs during the same instrument cycle. Table 2 illustrates a reorganization of the same time-templates shown in Table 1 which has the effect of allowing all time-templates to process simultaneously without the use of "inter-dummy" vessels while still requiring the 14 leading and trailing dummies at the expense of one extra revolution of the reaction wheel if time-template type 7 is included in the assay mix.

An example of one means to combine all assays from the Table 2 time-templates is now described. Assume that 100 assay requests have been made representing 20 requests from time-template types 7 and 10 requests from each of the other 8 time-templates. During the first 12 minutes of revolution 1, dispense the first two reagents (R1) and (R2) and or samples for each of the 40 time-template type 2, 6, 8, and 9 methods. During the next 24 minutes, index the reaction wheel to the starting position to begin revolution 2, i.e., the second cycle for time-templates 2, 6, 8, and 9, without performing any wash. During the next 12 minutes add samples and or reagents to each time-template types 2, 6, 8 and 9 assays already in progress. During the next 12 minutes, beginning with the 41st vessel, without the interspersion of any dummy vessels, dispense samples and or reagents for each of the 40 time-template type 1, 3, 4, and 5 assays. During the third 12 minutes of the second cycle, index the reaction wheel forward to the starting position to begin revolution 3 still without performing any wash. During the first 12 minutes of revolution 3 dispense the first two reagents (R1) and (R2), or nothing for time-template type 9 for each of the 40 time-template type 2, 6, 8, and 9 assays. During the next 12 minutes, beginning in the 41st vessel, dispense samples and/or reagents for each of the 40 time-template type 1, 3, 4, and 5 assays. During the next 6 minutes, beginning in the eighty-first vessel, without the interspersion of any dummy vessels, dispense reagents (R1) and (R2) for each of the 20 time-template type 7 assays. At the next step, or reaction wheel index, the leading vessel will be positioned at processing position 138 (the 101st processing position) and the first wash will begin. Seven leading dummy vessels will be created by the wash resource by the time the leading cup reaches position 162 and seven trailing dummy vessels will be created by the wash resource as the first wash continues by the time the 100th vessel reaches position 162. Processings continues as described in Table 2 with a wash and measurement occurring on all reaction vessels during one or more of revolutions 3 through 6 of the reaction wheel with the final revolution being the measurement of time-template 7 type assays.

An improvement upon the above means of operation using the common cycle first wash organization of time-templates given by Table 2 is described as follows. An object of the improvement is to decrease the time required to report results of assays started in the second revolution and to decrease the time some samples remain idle on the sample wheel. No improvement in the total time to complete a batch with a mix of all time-templates is sought nor is the system throughput as defined below actually improved.

In this improvement using the Table 2 organization a quantity Q1 equal to the reaction vessels required for all assays of time-template types 2, 6, 8 and 9 is determined. A quantity Q2 equal to the total number of vessels required for use by assays of time-template types 1, 3, 4, 5 is determined. A quantity Q3 equal to the total number of vessels required for use by assays of time-template type 7 is determined. The assays of time-template types 2, 6, 8 and 9 are begun in revolution 1 as the reaction wheel indexes through the first Q1 positions. The reaction wheel is then indexed normally to the 120 minus Q3 position where the assays of time-template types 1, 3, 4, and 5 are begun and continued using Q2 reaction vessels.

The reaction wheel then indexes 1 position to bring the first vessel into dispersing position 108 for the start of revolution 2. The first Q1 vessels are processed according to cycle 2 of their respective time-templates. The reaction wheel is indexed to the 120 minus Q3 vessel position and Q2 vessels are processed according to analysis cycle 2 of their respective time-templates. The reaction wheel then indexes 1 position to bring the first vessel into position 108 for the start of revolution 3. The first Q1 vessels are processed according to analysis cycle 3 of their respective time-templates. The reaction wheel is indexed to the 120 minus Q2 minus Q3 vessel position and Q3 vessels are processed according to analysis cycle 1 of time-template type 7. Q2 vessels are then processed according to analysis cycle 3 of their respective time-templates.

At this point in time-template type 7 vessels are now in the leading position on the reaction wheel followed by time-template types 1, 3, 4, and 5 followed by time-template types 2, 6, 8 and 9. In the previous description the order of the time-template groups was inverted. In this organization the results for time-template type 2 are produced at exactly the same time as in the previous embodiment. In this organization however, the results of time-template type 1 are produced before those of time-template type 2, unlike the the previous example where they were produced later. This increases the apparent throughput at the beginning of the batch and causes the samples of time-template types 2, 6, 8, 9 and 7 to remain idle slightly less time. This improvement is of practical value since frequently requested panels of results provided on the same sample frequently use both time-template types 1 and 2 and the total time to produce these panels is reduced slightly.

CONCLUSION

Multiple time-template method processing according to the two Table organizations described compare as follows, assuming, of course, batch processing with a maximum number of 120 reaction vessels. The Table 1 organization allows a maximum of 86 assays to be processed in six reaction wheel revolutions with the consumption of 28 dummy vessels while the Table 2 organization allows a maximum of 100 assays to be processed in seven reaction wheel revolutions with the consumption of 14 dummy vessels. Since the reaction vessels are disposable, single use commodities in the preferred embodiment the difference of 14 used vessels per batch between the two organizations can represent a significant operating cost differential.

If throughput is defined as the number of results produced divided by the number of hours required by the batch (using the exemplary times given) to produce all of those results, then the maximum throughput on a batch including assays of all time-templates is 86 assays divided by 3.6 hours which is 23.9 tests per hour for the Table 1 organization and 100 assays divided by 4.2 hours which is 23.8 assays per hour for the Table 2 organization. If time-template type 7 is eliminated from the mix of test requests, but a full reaction wheel load is maintained then the Table 1 organization will be able to process 93 assays using a total of just 21 dummy vessels so that its throughput will be given by 93 assays divided by 3.6 hours which is 25.8 assays per hour while the Table 2 organization yields a throughput of 100 assays divided by 3.6 hours which is 27.8 assays per hour. The throughput differences grow dramatically if the distance between probes in the wash station increases e.g. suppose the preferred embodiment of the split wash station was not used and only one gang wash assembly holding all seven probes was used, then 18 dummy reaction vessels would be required leading the first vessel and 18 trailing the last. Because leading and trailing dummy vessels can be the same physical vessels, a total of 20 dummy vessels would be created by both Table organizations. The Table 1 organization would however require 36 additional "inter-dummies" to process all method time-templates simultaneously thus reducing the reaction wheel capacity to 64 assays for a maximum throughput of 64 assays divided by 3.6 hours which is 17.8 assays per hour versus 23.8 assays per hour for the Table 2 organization.

These several time-templates depicted in Tables 1 and 2 may be routinely programmed and stored in a floppy disk for use by the CPU in the apparatus described. Nevertheless, in order to provide a full disclosure, the somewhat more complex time-templates of Table are further described in terms of flowcharts in FIGS. 6A and 6B. These flow charts may be used to facilitate programming the CPU.

DESCRIPTION OF FLOWCHART 6A

FIG. 6A is a flowchart depicting the logic decisions and operations that may be used for effecting the time-templating technique described in connection with the Table 2 time-template types in which the first wash occurs in the same cycle and split gang wash is used. In FIG. 6A, the first three blocks compute the number of assays or tests requested in the batch process for each similar group of time-templates. Q1 is the number of tests for time-template types 2, 6, 8 and 9. Q2 is the number of tests for time-template types 1, 3, 4, and 5 and Q3 is the total number of tests for time-template type 7. If Q1 is not greater than zero and Q2 is not greater than zero and Q3 is not greater than zero then the process ends since there are no assays to perform.

If Q1 is greater than zero then the first revolution of the reaction wheel begins with samples and/or reagents being dispensed for each of Q1 vessels according to analysis cycle 1 of time-template types 2, 6, 8 and 9. The reaction wheel then indexes in a stepwise fashion to position 120. No washing is performed. The system is ready to begin the second wheel revolution. At the next index of the reaction wheel, revolution 2 begins by performing analysis cycle 2 on Q1 vessels according to time-template types 2, 6, 8 and 9. If Q2 is greater than zero, then as soon as the first Q1 reaction vessels are finished with analysis cycle two, Q2 reaction vessels are processed according to analysis cycle 1 of time-template types 1, 3, 4 and 5. The leading vessel is indexed in a step wise fashion to position 120 and no washing is performed. The system is ready to begin the third wheel revolution for the third analysis cycle of the batch. At the next index of the reaction wheel, revolution 3 begins by performing analysis cycle three on Q1 vessels according to time-template types 2, 6, 8 and 9. If Q2 is greater than zero then as soon as the first Q1 reaction vessels are finished with analysis cycle three, Q2 reaction vessels are processed according to analysis cycle 2 of time-template types 1, 3, 4 and 5. If Q3 is greater than zero then as soon as the first Q1 plus Q2 reaction vessels are finished dispensing, Q3 reaction vessels are processed according to analysis cycle 1 of time-template type 7. The leading vessel is indexed in a step wise fashion to position 100. The first wash is begun and continues for all vessels on the reaction wheel. The next wheel revolution begins when the leading vessel reaches reaction position 1, i.e., the numeral 108 in FIG. 3. The next analysis cycle is completed on all vessels according to the time-template type. If all assays are not complete, the reaction wheel goes through another revolution with the next analysis cycle of incomplete assays being performed; otherwise the process ends.

If on the other hand Q1 is not greater than zero and Q2 is greater than zero then the first wheel revolution begins with samples and/or reagents being dispensed for each of Q2 vessels according to analysis cycle 1 of time-template types 1, 3, 4 and 5. The leading vessel is indexed in a step-wise fashion for 120 positions and no washing is performed. The system is ready to begin the second wheel revolution. At the next index of the reaction wheel, revolution 2 begins by performing analysis cycle 2 on Q2 vessels according to time-template types 1, 3, 4 and 5. If Q3 is greater than zero then as soon as the first Q2 reaction vessels are finished with analysis cycle two, Q3 reaction vessels are processed according to analysis cycle 1 of time-template type 7. The leading vessel is indexed 100 steps in a step-wise fashion to processing position 136 (FIG. 3). The first wash is begun and continues for all vessels on the reaction wheel. The next wheel revolution begins when the leading vessel reaches position 108. The next analysis cycle on all vessels is carried out according to the time-template type and to the reagent in each vessel. If all assays are not complete, the reaction wheel goes through another revolution with the next analysis cycle of incomplete assays being performed otherwise the process ends.

If on the other hand only Q3 is greater than zero, then the first reaction wheel revolution begins with samples and or reagents being dispensed for each of Q3 vessels according to analysis cycle 1 of time-template type 7. The leading vessel is indexed 100 steps to processing position 136 (FIG. 3). The first wash begins with the next index of the reaction wheel. The next wheel revolution begins when the leading vessel reaches processing position 108 (FIG. 3). The next analysis cycle on all vessels according to the time-template type and to the method in each vessel is carried out. If all assays are not complete, the reaction wheel goes through another revolution with the next analysis cycle of incomplete assays being performed; otherwise the process ends.

DESCRIPTION OF FLOWCHART 6B

Figures 1, 6B:
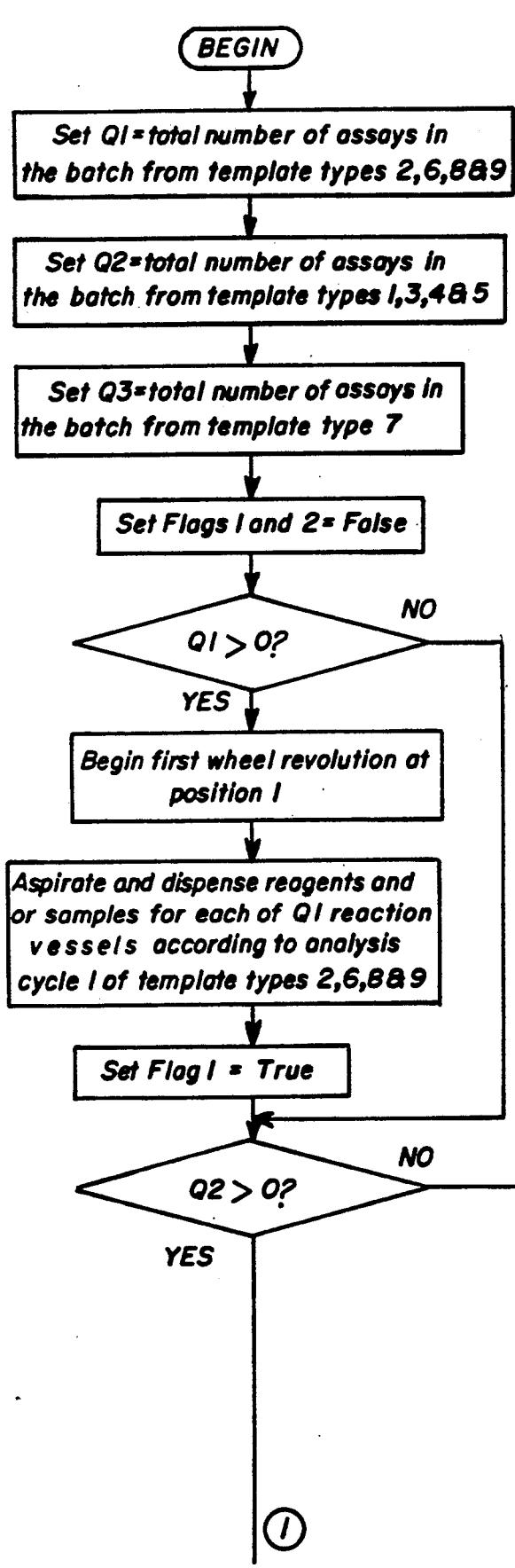
Figures 2, 6B:
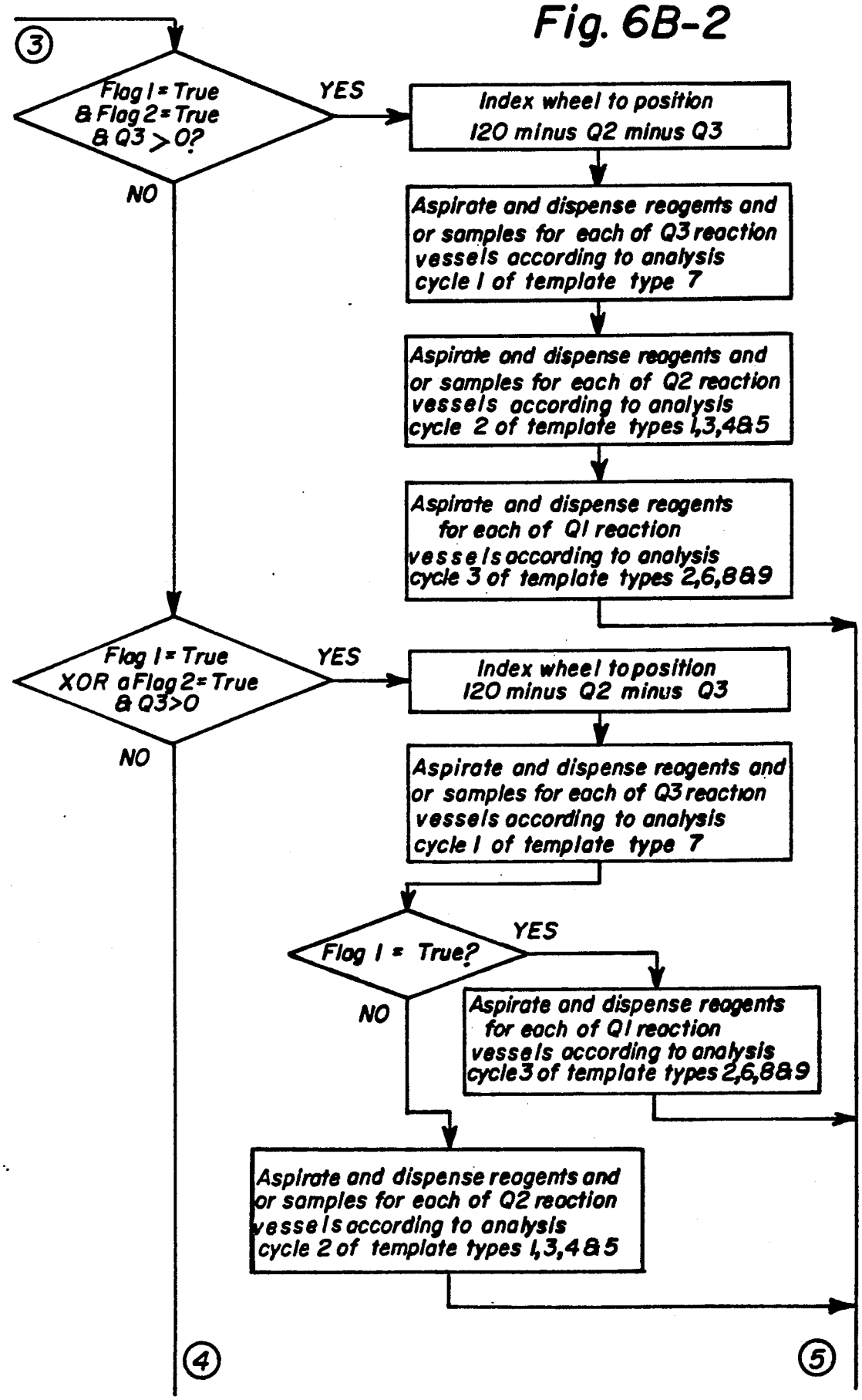
Figures 3, 6B:
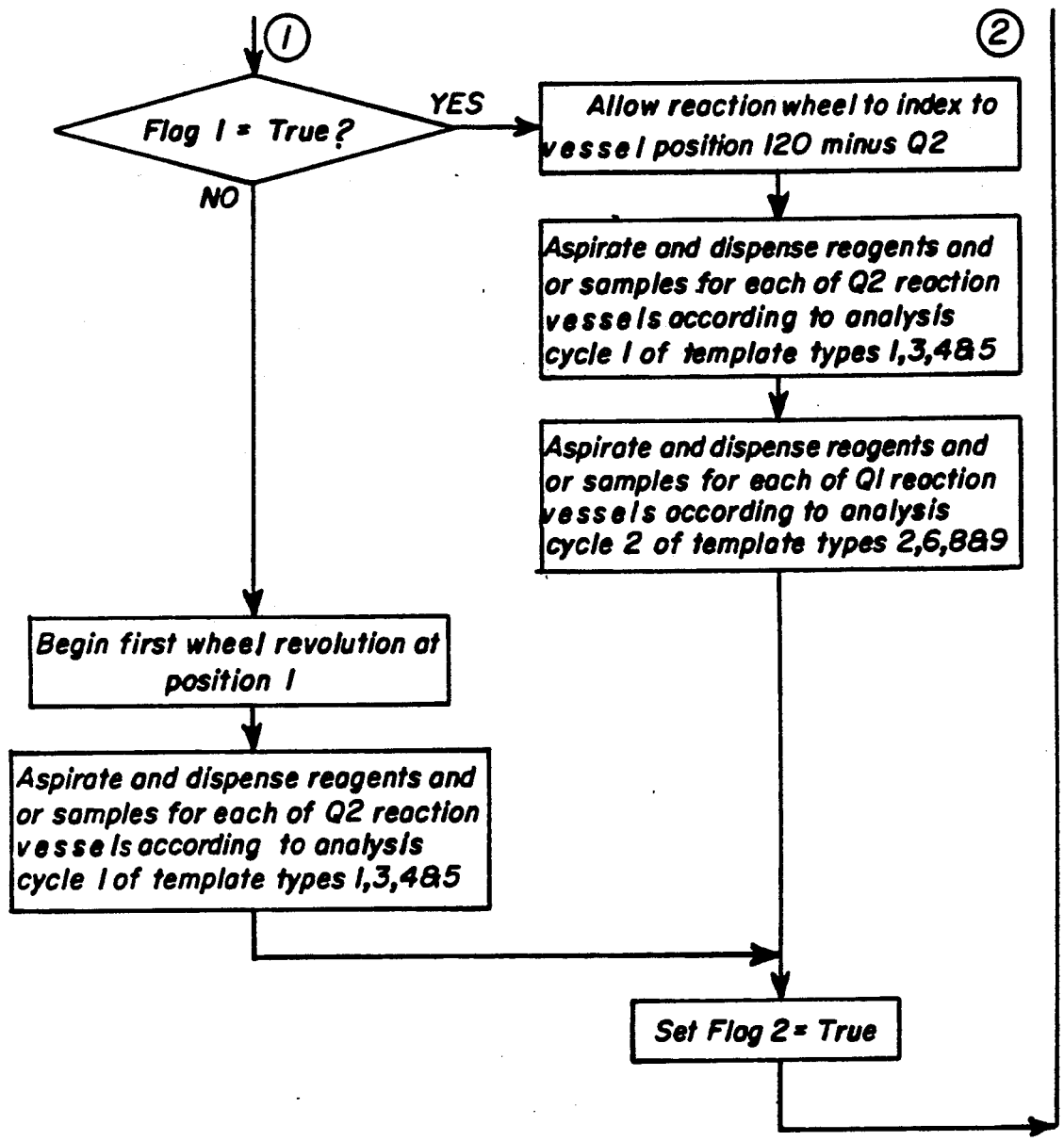
Figures 4, 6B:
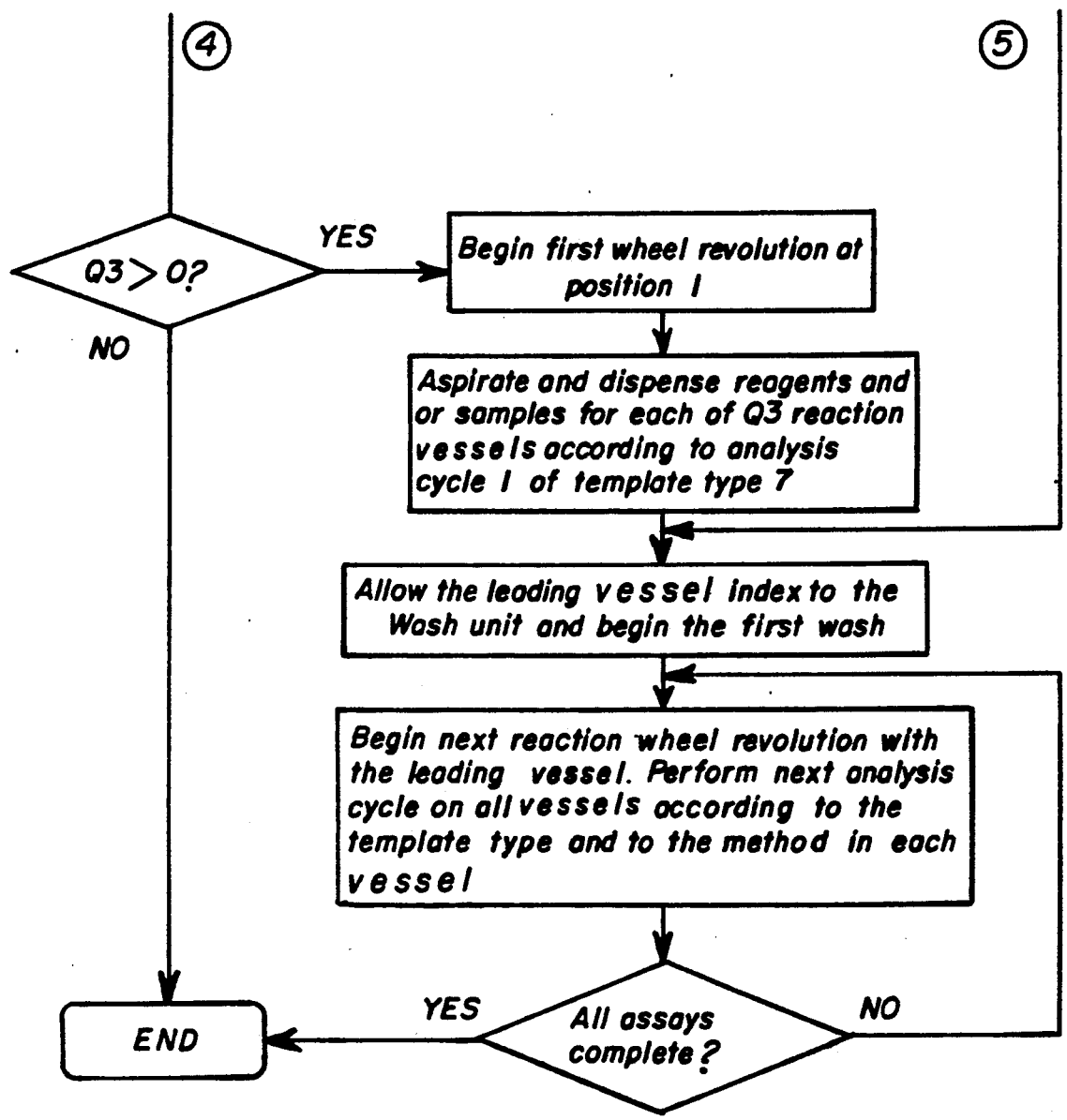

FIG. 6B is a flowchart depicting the logic decisions and operations that may be used for the improved time-templating technique described above in connection with the Table 2 time-template type in which the first wash occurs in the same cycle and split gang wash elements are used. In FIG. 6B, the first three blocks compute the number of assays or tests requested in the batch for each similar group of time-templates. Q1 is the number of tests for time-template types 2, 6, 8 and 9. Q2 is the number of tests for time-template types 1, 3, 4, and 5 and Q3 is the total number of tests for time-template type 7. Software flags 1 and 2 are set equal to False conditions signifying that no assays have begun to run.

If Q1 is not greater than zero, then the system branches to check the value of Q2, otherwise the first revolution of the reaction wheel begins at processing position 108 (FIG. 3). The first reaction cycle is begun for each of Q1 vessels with analysis cycle 1 from time-templates 2, 6, 8 and 9. Flag 1 is set to True, indicating that the above operations have taken place.

If Q2 is not greater than zero then the system branches to check if other testing is in progress, other wise a check of Flag 1 status is made. If Flag 1 is False, indicating no time-template 2, 6, 8 or 9 methods are in progress, then the first reaction wheel revolution begins at position 1 for each of Q2 vessels with analysis cycle 1 from time-templates 1, 3, 4 and 5. Flag 2 is then set True. If Flag 1 was true however, the first wheel revolution is allowed to progress to vessel position 120 minus Q2 where analysis cycle one from time-templates 1, 3, 4 and 5 for each of Q2 vessels is begun. Since these Q2 vessels are immediately in front of the Q1 vessels in progress, the next step is to begin analysis cycle 2 on Q1 vessels of time-templates 2, 6, 8, and 9. Flag 2 is then set True.

Whether Flag 2 is set or not, a check is then made to determine if Flag 1 and Flag 2 are both True and if Q3 is also greater than zero. If the check is true then the reaction wheel indexes to vessel position 120 minus Q2 minus Q3 where analysis cycle one of all methods in time-template type 7 on Q3 vessels is begun. Since these vessels immediately precede the Q2 vessels, analysis cycle 2 is performed on Q2 vessels. Since these precede the Q1 vessels, analysis cycle 3 is performed on Q1 vessels. The process continues by allowing the leading vessel to index to the first wash position, and then perform the first wash on all vessel. The next reaction wheel revolution is then begun, performing the next analysis cycle appropriate to each vessel. At the end of this revolution a check is made to determine if all assays are complete. If they are complete, the batch ends, If not, the next revolution and analysis cycle are begun.

If "Flag 1 and Flag 2 are both True and if Q3 is also greater than 0" is not a true statement, then a check is made to determine if either Flag 1 or Flag 2, but not both, are true and Q3 is greater than zero. If the check is true then the reaction wheel indexes to vessel position 120 minus Q2 minus Q3 where analysis cycle 1 of all methods in time-template type 7 on Q3 vessels is begun. If flag 1 is True then analysis cycle 3 is begun on the Q1 vessels for methods in time-template types 2, 6, 8 and 9. The process continues by allowing the leading vessel to index to the first wash position, and then perform the first wash on all vessels. The next reaction wheel revolution is then begun, performing the next analysis cycle appropriate to each vessels. At the end of this revolution a check is made to determine if all assays are complete. If they are complete, the batch ends, If not, the next revolution and analysis cycle are begun. If however, Flag 1 is False then analysis cycle 2 is begun on Q1 vessels for methods in time-template types 1, 3, 4 and 5. The process continues by allowing the leading vessel to index to the first wash position, and then perform the first wash on all vessels. The next reaction wheel revolution is then begun, performing the next analysis cycle appropriate to each vessel. At the end of this revolution, a check is made to determine if all assays are complete. If they are complete, the batch ends. If not, the next reaction wheel revolution and analysis cycle are begun.

If neither Flag 1 nor Flag 2 were True, then a check is made to determine if Q3 is greater than zero. If not, the batch ends. If it is greater than zero, then the first reaction wheel revolution begins at the first reaction vessel where analysis cycle 1 of all methods in time-template type 7 on Q3 vessels is begun. The process continues by allowing the leading vessel to index to the first wash position, and then perform the first wash on all vessels. The next reaction wheel revolution is then begun, performing the next analysis cycle appropriate to each vessel. At the end of this revolution a check is made to determine if all assays are complete. If they are complete, the batch ends, If not, the next revolution and analysis cycle are begun.

Figure 7:
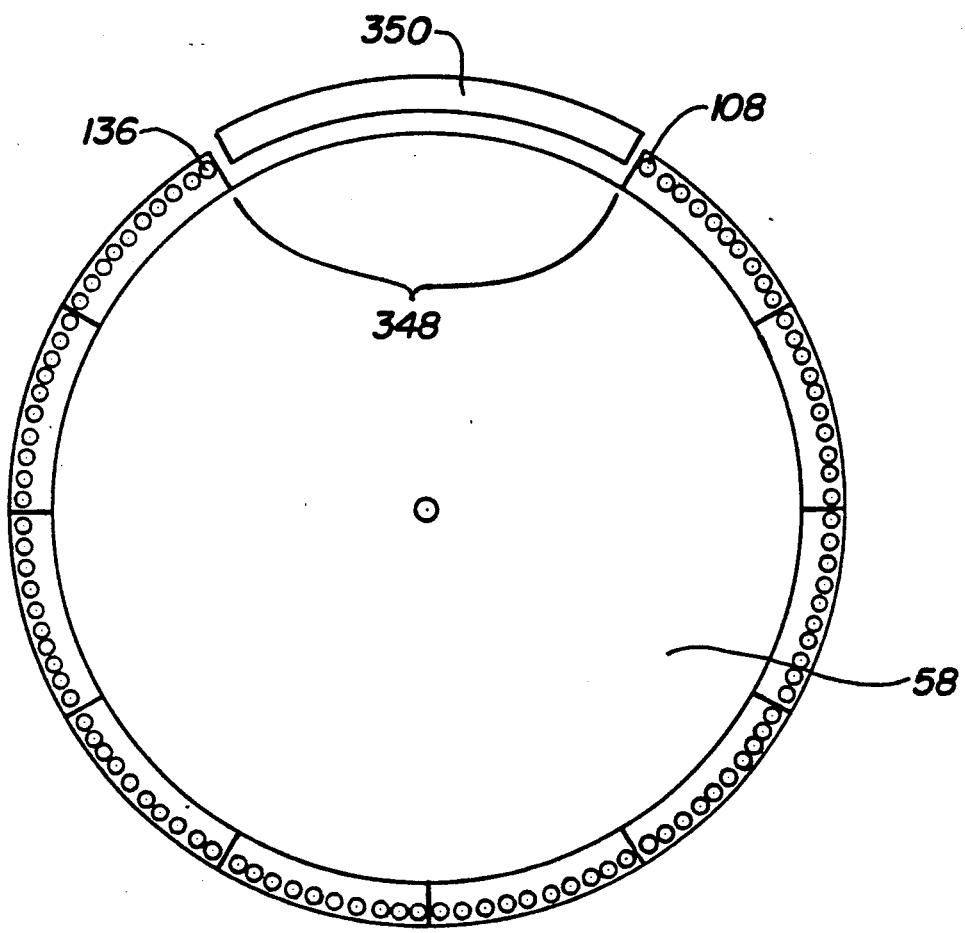
FIG. 7 is a plain view of an alternative embodiment of the reaction wheel and wash that may be used with the apparatus of FIG. 1.

FIG. 7 illustrates a further improvement in the gang wash concept. Given that the apparatus and method of this invention always use dummy reaction vessels in the position just ahead of the first reaction vessel, these dummy vessels may be eliminated from the reaction wheel 58 with the creation of an empty space or slot 348 in the wheel. A receptacle or other device to receive wash fluid 350 is be placed under the vessels in the wash station area in order to receive fluids that would otherwise consume the dummy vessels. A drain (not shown) to convey such wash fluids to a waste container is also provided. With the slot 348 in the position shown, the first reagent or sample dispense of the first wheel revolution occurs at position 108 only when the wheel is rotated so that the vessel shown in processing position 136 is brought into processing position 108. The advantages of this improvement are that the loss of the disposable reaction vessels used as dummy vessels is avoided as is the time required to load and unload them.

While the invention has been described in an exemplary embodiment using particular numbers of reaction vessels, rotation speeds for the reaction wheel, types of time-templates, magnetic particles for the solid support, and heterogeneous immunoassays, it is to be understood the invention is not so limited. The principles and advantages of the split gang wash, dummy reaction vessels, and time-templates in which there is a simultaneous first wash are the subject matter of the several claims.

What is claimed is:

1. In an automatic analytical apparatus for performing immunoassays on samples using a solid support, the assays having bound and free phases, the bound phase being bound to the solid support, the apparatus having a plurality of reaction vessels with a solid support, and having a plurality of sequentially located processing positions, means to stepwise index the reaction vessels in sequence to several processing positions for an analysis cycle, the index means effecting at least two cycles, the positions having means to add samples and/or reagents, to incubate, to wash, or to measure the contents of the vessels, the improvement wherein:

the wash means includes at least two wash probes for aspirating or dispensing liquids, coupled for simultaneous insertion into a different one of said reaction vessels spaced apart at least one of said processing positions, time template means constructed so as to control a different set of immunoassays to effect first use of the wash means in the same cycle, the index means, positioned and arranged so as to be controlled by said time template means, and constructed for indexing said reaction vessels uniformly with respect to time, the index means is a continuous loop with said reaction vessels locate about the periphery of the loop, the loop having a peripheral sector being constructed so as not to receive a number of said reaction vessels, corresponding to the processing positions between the insertable wash probes.

2. The apparatus set forth in claim 1 wherein the means for adding sample and/or reagents is constructed so as to disable each cycle for a number of vessels leading and/or trailing first and last vessels receiving sample or reagent, said number of vessels corresponding to the number of processing positions between the insertable wash probes.

3. A method for performing multiple types of heterogeneous immunoassays on at least one sample using solid supports, the assays having bound and free phases with the bound phase bound to the solid support, and a plurality of reaction vessels comprising the steps of:

performing multiple time templates each comprising indexing, during a cycle, the reaction vessels to successive processing positions at which alternatively and/or simultaneously sample and/or reagents are added to the vessels and/or mixed, and/or the vessels are washed using wash means, and/or the contents of the vessels are incubated and/or measured, repeating the cycle, and simultaneously during each cycle inserting the wash means into different, spaced vessels while these vessels are carrying out different immunoassays, and the reaction vessels being indexed over plural cycles according to a different one of said time-templates for the respective immunoassays under which said time-templates the first vessel washing occurs in the same cycle.

4. The method of claim 3, further comprising, inserting said wash means into all time templates during each cycle subsequent to the first insertion of said wash means.

* * * * *